(12) United States Patent
Tabuteau

(10) Patent No.: US 9,034,889 B2
(45) Date of Patent: *May 19, 2015

(54) COMPOSITIONS FOR ORAL ADMINISTRATION OF ZOLEDRONIC ACID OR RELATED COMPOUNDS FOR TREATING LOW BACK PAIN

(71) Applicant: Antecip Bioventures II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/279,229

(22) Filed: May 15, 2014

(65) Prior Publication Data

US 2014/0249112 A1 Sep. 4, 2014

Related U.S. Application Data

(63) Continuation of application No. 14/063,979, filed on Oct. 25, 2015, now Pat. No. 8,802,658, which is a continuation-in-part of application No. 13/894,274, filed on May 14, 2013.

(60) Provisional application No. 61/646,538, filed on May 14, 2012, provisional application No. 61/647,478, filed on May 15, 2012, provisional application No. 61/654,092, filed on Jun. 1, 2012, provisional application No. 61/654,383, filed on Jun. 1, 2012, provisional application No. 61/655,527, filed on Jun. 5, 2012, provisional application No. 61/655,541, filed on Jun. 5, 2012, provisional application No. 61/764,563, filed on Feb. 14, 2013, provisional application No. 61/762,225, filed on Feb. 7, 2013, provisional application No. 61/767,647, filed on Feb. 21, 2013, provisional application No. 61/767,676, filed on Feb. 21, 2013, provisional application No. 61/803,721, filed on Mar. 20, 2013.

(51) Int. Cl.
| | | |
|---|---|---|
| A61K 31/675 | (2006.01) | |
| A61K 9/20 | (2006.01) | |
| A61K 9/28 | (2006.01) | |
| A61K 9/00 | (2006.01) | |

(52) U.S. Cl.
CPC ............. *A61K 31/675* (2013.01); *A61K 9/2004* (2013.01); *A61K 9/0053* (2013.01); *A61K 9/28* (2013.01); *A61K 9/20* (2013.01)

(58) Field of Classification Search
CPC ................. A61K 31/675; A61K 9/00
USPC ....................................................... 514/275
See application file for complete search history.

(56) References Cited

U.S. PATENT DOCUMENTS

| | | | |
|---|---|---|---|
| 7,888,345 B2 * | 2/2011 | Hoyt et al. ............... | 514/212.07 |
| 2004/0063670 A1 | 4/2004 | Fox et al. | |
| 2010/0215743 A1 | 8/2010 | Leonard | |
| 2011/0028435 A1 | 2/2011 | Hanna et al. | |
| 2011/0098252 A1 * | 4/2011 | Pappagallo ...................... | 514/94 |
| 2012/0190647 A1 | 7/2012 | Hanna et al. | |
| 2013/0274282 A1 | 10/2013 | Tabuteau | |
| 2013/0303485 A1 | 11/2013 | Tabuteau | |
| 2013/0303486 A1 | 11/2013 | Tabuteau | |
| 2013/0303487 A1 | 11/2013 | Tabuteau | |
| 2013/0303488 A1 | 11/2013 | Tabuteau | |
| 2014/0051669 A1 | 2/2014 | Tabuteau | |
| 2014/0051718 A1 | 2/2014 | Tabuteau | |
| 2014/0249107 A1 | 9/2014 | Tabuteau | |
| 2014/0249109 A1 | 9/2014 | Tabuteau | |
| 2014/0249111 A1 | 9/2014 | Tabuteau | |
| 2014/0249112 A1 | 9/2014 | Tabuteau | |
| 2014/0249113 A1 | 9/2014 | Tabuteau | |
| 2014/0249317 A1 | 9/2014 | Tabuteau | |

FOREIGN PATENT DOCUMENTS

| | | |
|---|---|---|
| WO | 2002087555 | 11/2002 |
| WO | WO 2005005447 A2 * | 1/2005 |
| WO | 2005063218 | 7/2005 |
| WO | 2005/107751 A1 | 11/2005 |
| WO | 2012071517 | 5/2012 |

OTHER PUBLICATIONS

Studies of bioavailability and food effects of MER-101 zoledronic acid tablets in postmenopausal women, 2009 Breast Cancer Symposium, Published on Meeting Library (http://meetinglibrary.asco.org).*

Ying Wang1, Rebekka Gehringer1, Shaaban A. Mousa2, Dagmar Hackel1, Alexander Brack1, Heike L. Rittner1, CXCL10 Controls Inflammatory Pain via Opioid Peptide-Containing Macrophages in Electroacupuncture, PLOS One, Apr. 2014 | vol. 9 | Issue 4 | e94696.*

Tamara King and Frank Porreca, Preclinical Assessment of Pain: Improving Models in Discovery Research, Curr Topics Behav Neurosci (2014) 20: 101-120.*

Laslett, Extended report: Zoledronic acid reduces knee pain and bone marrow lesions over 1 year: a randomized controlled trial. Ann. Rheum. Dis. 2012, 71: 1322-1328.

Bertorelli et al., Nociceptin and the ORL-1 ligand [Phe1(CH2-NH)Gly2]nociceptin(1-13)NH2 exert anti-opioid effects in the Freund's adjuvant-induced arthritic rat model of chronic pain. British Journal of Pharmacology (1999) 128, 1252-1258.

Bingham III et al., Risedronate decreases biochemical markers of cartilage degradation but does not decrease symptoms or slow radiographic progression in patients with medical compartment osteoarthritis of the knee. Arthritis & Rheumatism, vol. 54, No. 11, 2006, 3494-3507.

(Continued)

*Primary Examiner* — Kendra D Carter
*Assistant Examiner* — Jason A Deck
(74) *Attorney, Agent, or Firm* — K&L Gates LLP; Louis C. Cullman; Brent A. Johnson

(57) ABSTRACT

Oral dosage forms of bisphosphonate compounds, such as zoledronic acid, can be used to treat or alleviate pain or related conditions. The oral bioavailabilty of zoledronic acid can be enhanced by administering the zoledronic acid in the disodium salt form.

15 Claims, 10 Drawing Sheets

(56) References Cited

OTHER PUBLICATIONS

Cullen et al., MER-101: A bioavailability study of various GIPET formulations in beagle dogs with intraduodenal cannulae. Poster Presentation, Nov. 2007.
De Castro et al., Zoledronic acid to treat complex regional pain syndrome type I in adult (case report). Rev. Dor. Sao Paulo, 2011, 12(1): 71-73.
EU Product Label for Zometa, accessed 2013.
Giles, Risedronate not an Effective Disease Modifier in Knee Osteoarthritis. Arthritis News (website) 2006. Accessed at http://www.hopkinsarthritis.org/arthritis-news/risedronate-not-an-effective-disease-modifier-in-knee-osteoarthritis.
Guo et al., Substance P signaling contributes to the vascular and nociceptive abnormalities observed in a tibial fracture rat model of complex regional pain syndrome type I. Pain 108 (2004) 95-107.
Kingery et al., A substance P receptor (NK1) antagonist can reverse vascular and nociceptive abnormalities in a rat model of complex regional pain syndrome type II. Pain 104 (2003) 75-84.
Leonard et al., MER-101 Tablets: A pilot bioavailability study of a novel oral formulation of zoledronic acid. Poster Presentation, Oct. 2007.
Leonard et al., Safety Profile of Zoledronic acid in a novel oral formulation. Poster Presentation, Nov. 2009.
Leonard et al., Studies of bioavailability and food effects of MER-101 Zoledronic Acid Tablets in Postmenopausal Women. Poster Presentation, Oct. 2009.
McHugh et al., MER-101-03, A multi center, phase II study to compare MER-101 20mg tablets to intravenous Zometa 4mg in prostate cancer patients. Poster Presentation, May 2009.
Nagae et al., Acidic microenvironment created by osteoclasts causes bone pain associated with tumor colonization. J. Bone Miner. Metab. (2007) 25: 99-104.
Nagae et al., Osteoclasts play a part in pain due to the inflammation adjacent to bone. Bone 39 (2006) 1107-1115.
Nagakura et al., Allodynia and hyperalgesia in adjuvant-induced arthritic rats: time course of progression and efficacy of analgesics. The Journal of Pharmacology and Experimental Therapeutics 306: 490-497, 2003.
Orazol(R): Novel approach to adjuvant therapy for improving outcomes in breast cancer. Merrion Pharmaceuticals, accessed 2013.
Reid et al., Intravenous Zoledronic Acid in Postmenopausal Women with Low Bone Mineral Density. N. Engl. J. Med., vol. 346, No. 9, 2002.
Ringe et al., A review of bone pain relief with ibandronate and other bisphosphonates in disorders of increased bone turnover. Clin. Exp. Rheumatol. 2007; 25: 766-774.
Study: The Use of Zoledronic Acid to Complex Regional Pain Syndrome (Aclasta) sponsored by University of Sao Paulo General Hospital. 2012. Clinical Trials.gov. Accessed on Apr. 5, 2013 at http://clinicaltrials.gov/ct2/show/ NCT01788176.
US Product Label for Zometa, accessed 2013.
Walker et al., Disease modifying and anti-nociceptive effects of the bisphosphonate, zoledronic acid in a model of bone cancer pain. Pain 100 (2002) 219-229.
Zaspel et al., Treatment of early stage CRPS I—cortisone (methylprednisolone) versus bisphosphonate (zoledronic acid). German Congress of Orthopedics and Traumatology. 71st Annual Meeting of the German Society of Trauma Surgery, 93rd Meeting of the German Society for Orthopedics and Orthopedic Surgery, 48th Meeting of the Professional Association of Specialists in Orthopedics. Berlin, Oct. 24-27, 2007. German Medical Science GMS Publishing House; 2007.
Zoledronate Disodium: Treatment of Tumor-Induced Hypercalcemia Angiogenesis Inhibitor, Drugs of the Future 2000, 25(3) 259-268.
Zometa FDA Pharmacology Review, part 1, accessed 2013.
Zometa FDA Pharmacology Review, part 2, accessed 2013.
Zometa FDA Pharmacology Review, part 3, accessed 2013.
Zometa FDA Pharmacology Review, part 4, accessed 2013.
Zometa FDA Pharmacology Review, part 5, accessed 2013.
Sebastin, Complex rgional pain syndrome, Indian J. Past Surg., 4492): 298-307 (2011.
Ringe "Development of clinical utility of zoledronic acid and patient consideration in the treatment of osteoporosis." Patient Preference and Adherence 2010:4 231-245.
Chandler, Labeling of unit dose packages of drugs, Department of Pharmacy Policy, University of Kentucky Hospital, Chandler Medical Center, policy No. PH-04-06, 2009.
Committee for Orphan Medicinal Products (COMP) meeting report on the review of applications for orphan designation, European Medicines Agency, Sep. 2013.
Conte, et al., The Oncologist 2004:9(Supp 4):28-37.
English, A life of pain: woman chooses amputation to deal with painful disorder. Http://www.katu.com/news/loca.A-life-of-pain-woman-chooses amputation-to-deal with . . . Nov. 18, 2013.
FDA Approved medication Guide-Reclast (zoledronic acid) injection, Aug. 2011.
http://cancerguide.org/drugdosing.html, Page Created: 2000, last Updated: Sep. 22, 2000.
Opinion of the Committee for Orphan Medicinal Products on orphan medicinal product designation, European Medicines Agency, Sep. 2013, pp. 1-3.
FDA Severe Pain with Osteoporosis drugs, Mar. 2008, FDA patient safety news: Show #73.
Reclast Label, Revised: Aug. 2011, Novartis Pharma Stein AG.
Scientific Discussion. EMEA 2005, pp. 1-24.
Zometa Label, Revised: Mar. 2012, Novartis Pharma Stein AG.
U.S. Appl. No. 14/495,732, filed Jan. 26, 2015 First Named Inventor: Herriot Tabuteau Assignee: Antecip Bioventures II LLC.
U.S. Appl. No. 14/481,097, filed Sep. 9, 2014 First Named Inventor: Herriot Tabuteau Assignee: Antecip Bioventures II LLC.
U.S. Appl. No. 14/538,709, filed Nov. 11, 2014 First Named Inventor: Herriot Tabuteau Assignee: Antecip Bioventures II LLC.
U.S. Appl. No. 14/530,556, filed Oct. 31, 2014 First Named Inventor: Herriot Tabuteau Assignee: Antecip Bioventures II LLC.
U.S. Appl. No. 14/536,526, filed Jan. 28, 2015 First Named Inventor: Herriot Tabuteau Assignee: Antecip Bioventures II LLC.
U.S. Appl. No. 14/540,333, filed Nov. 13, 2014 First Named Inventor: Herriot Tabuteau Assignee: Antecip Bioventures II LLC.
U.S. Appl. No. 14/604,524, filed Jan. 23, 2015 First Named Inventor: Herriot Tabuteau Assignee: Antecip Bioventures II LLC.
U.S. Appl. No. 14/605,822, filed Jan. 26, 2015 First Named Inventor: Herriot Tabuteau Assignee: Antecip Bioventures II LLC.
U.S. Appl. No. 14/607,947, filed Jan. 28, 2015 First Named Inventor: Herriot Tabuteau Assignee: Antecip Bioventures II LLC.
U.S. Appl. No. 14/607,985, filed Jan. 28, 2015 First Named Inventor: Herriot Tabuteau Assignee: Antecip Bioventures II LLC.
U.S. Appl. No. 13/894,244, filed May 14, 2013 First Named Inventor: Herriot Tabuteau Assignee: Antecip Bioventures II LLC.
U.S. Appl. No. 13/894,252, filed May 14, 2013 First Named Inventor: Herriot Tabuteau Assignee: Antecip Bioventures II LLC.
U.S. Appl. No. 13/894,262, filed May 14, 2013 First Named Inventor: Herriot Tabuteau Assignee: Antecip Bioventures II LLC.
U.S. Appl. No. 13/894,274, filed May 14, 2013 First Named Inventor: Herriot Tabuteau Assignee: Antecip Bioventures II LLC.
U.S. Appl. No. 14/106,291, filed Dec. 13, 2013 First Named Inventor: Herriot Tabuteau Assignee: Antecip Bioventures II LLC.
U.S. Appl. No. 14/279,196, filed May 15, 2014 First Named Inventor: Herriot Tabuteau Assignee: Antecip Bioventures II LLC.
U.S. Appl. No. 14/279,206, filed May 15, 2014 First Named Inventor: Herriot Tabuteau Assignee: Antecip Bioventures II LLC.
U.S. Appl. No. 14/279,213, filed May 15, 2014 First Named Inventor: Herriot Tabuteau Assignee: Antecip Bioventures II LLC.
U.S. Appl. No. 14/279,222, filed May 15, 2014 First Named Inventor: Herriot Tabuteau Assignee: Antecip Bioventures II LLC.
U.S. Appl. No. 14/279,226, filed May 15, 2014 First Named Inventor: Herriot Tabuteau Assignee: Antecip Bioventures II LLC.
U.S. Appl. No. 14/279,229, filed May 15, 2014 First Named Inventor: Herriot Tabuteau Assignee: Antecip Bioventures II LLC.
U.S. Appl. No. 14/279,232, filed May 15, 2014 First Named Inventor: Herriot Tabuteau Assignee: Antecip Bioventures II LLC.
U.S. Appl. No. 14/279,241, filed May 15, 2014 First Named Inventor: Herriot Tabuteau Assignee: Antecip Bioventures II LLC.

(56) References Cited

OTHER PUBLICATIONS

U.S. Appl. No. 14/279,236, filed May 15, 2014 First Named Inventor: Herriot Tabuteau Assignee: Antecip Bioventures II LLC.
U.S. Appl. No. 14/336,642, filed Jul. 21, 2014 First Named Inventor: Herriot Tabuteau Assignee: Antecip Bioventures II LLC.
U.S. Appl. No. 14/456,939, filed Aug. 11, 2014 First Named Inventor: Herriot Tabuteau Assignee: Antecip Bioventures II LLC.
U.S. Appl. No. 14/457,659, filed Aug. 12, 2014 First Named Inventor: Herriot Tabuteau Assignee: Antecip Bioventures II LLC.
U.S. Appl. No. 14/625,457, filed Feb. 18, 2015 First Named Inventor: Herriot Tabuteau Assignee: Antecip Bioventures II LLC.
U.S. Appl. No. 14/635,857, filed Mar. 2, 2015 First Named Inventor: Herriot Tabuteau Assignee: Antecip Bioventures II LLC.
U.S. Appl. No. 14/639,013, filed Mar. 4, 2015 First Named Inventor: Herriot Tabuteau Assignee: Antecip Bioventures II LLC.
ISR & Written Opinion for PCT/US2014/050427, mailed Nov. 20, 2014.

* cited by examiner

COMPOSITIONS FOR ORAL ADMINISTRATION OF ZOLEDRONIC ACID OR RELATED COMPOUNDS FOR TREATING LOW BACK PAIN

CROSS-REFERENCE TO RELATED APPLICATIONS

This application is a continuation of U.S. patent application Ser. No. 14/063,979, filed Oct. 25, 2013, which is a continuation-in-part of U.S. patent application Ser. No. 13/894,274, filed May 14, 2013, which embodiments the benefit of U.S. Provisional Applications 61/646,538, filed May 14, 2012; 61/647,478, filed May 15, 2012; 61/654,292, filed Jun. 1, 2012; 61/654,383, filed Jun. 1, 2012; 61/655,527, filed Jun. 5, 2012; 61/655,541, filed Jun. 5, 2012; 61/764,563, filed Feb. 14, 2013; 61/762,225, filed Feb. 7, 2013; 61/767,647, filed Feb. 21, 2013; 61/767,676, filed Feb. 21, 2013; and 61/803,721, filed Mar. 20, 2013, all of which are incorporated by reference in their entirety herein.

BACKGROUND

Bisphosphonate compounds are potent inhibitors of osteoclast activity, and are used clinically to treat bone-related conditions such as osteoporosis and Paget's disease of bone; and cancer-related conditions including multiple myeloma, and bone metastases from solid tumors. They generally have low oral bioavailability.

SUMMARY

It has been discovered that oral dosage forms of bisphosphonate compounds, such as zoledronic acid, can be used to treat or alleviate pain or related conditions.

Some embodiments include a method of enhancing the oral bioavailability of zoledronic acid comprising orally administering a dosage form containing zoledronic acid in the disodium salt form.

Some embodiments include a dosage form comprising zoledronic acid in the disodium salt form, wherein the bioavailability, in a mammal, of zoledronic acid in the disodium salt form is greater than the bioavailability of zoledronic acid in the diacid form would be in the same dosage form.

Some embodiments include a dosage form comprising zoledronic acid in the disodium salt form, wherein the dosage form contains an amount of zoledronic acid in the disodium salt form that provides an area under the plasma concentration curve of zoledronic acid of about 4 ng·h/mL to about 2000 ng·h/mL to a human being to which the dosage form is administered.

Some embodiments include a dosage form comprising zoledronic acid in the disodium salt form, wherein the disodium salt form is present in a lower molar amount than would be present if the zoledronic acid were in the diacid form; and wherein the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

Although an oral dosage form with enhanced bioavailability with respect to the bisphosphonate compound can be used, the treatment can also be effective using an oral dosage form that includes a bisphosphonate compound, such as zoledronic acid, wherein the bioavailability of the bisphosphonate is unenhanced, or is substantially unenhanced.

Some embodiments include a method of relieving inflammatory pain comprising administering an oral dosage form containing zoledronic acid to a mammal in need thereof, wherein the mammal experiences significant pain relief more than 3 hours after administration of the dosage form.

Some embodiments include a method of relieving pain associated with an arthritis comprising administering an oral dosage form containing zoledronic acid to a human being in need thereof.

Some embodiments include a method of treating complex regional pain syndrome comprising administering an oral dosage form containing zoledronic acid to a mammal in need thereof.

Some embodiments include an oral dosage form comprising zoledronic acid, wherein the oral bioavailability of zoledronic acid is substantially unenhanced. For example, in some embodiments, the oral bioavailability in the dosage form is about 0.01% to about 4%.

Some embodiments include a pharmaceutical product comprising more than one unit of an oral dosage form described herein. In some embodiments, each unit of the oral dosage form contains about 1 mg to about 50 mg of zoledronic acid.

Some embodiments include a method of relieving inflammatory pain comprising administering an oral dosage form containing zoledronic acid to a mammal in need thereof.

In some embodiments, the mammal receives a total monthly dose of zoledronic acid that is about 800 $mg/m^2$ or less.

In some embodiments, the dosage form contains about 10 $mg/m^2$ to about 20 $mg/m^2$ based upon the body surface area of the mammal.

Some embodiments include a method of relieving inflammatory pain comprising orally administering zoledronic acid to a mammal in need thereof.

In some embodiments, about 300 $mg/m^2$ to about 600 $mg/m^2$ of zoledronic acid is administered per month, based upon the body surface area of the mammal.

In some embodiments, about 50 $mg/m^2$ to about 600 $mg/m^2$ of zoledronic acid is administered per month, based upon the body surface area of the mammal.

DETAILED DESCRIPTION

Figure 1:
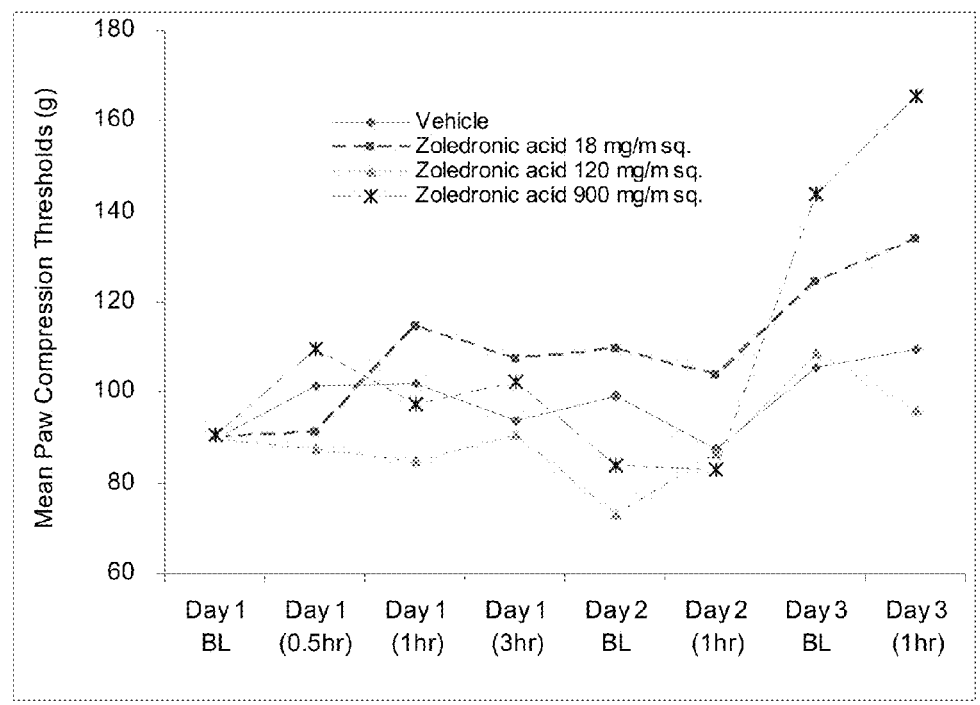
FIG. 1 is a plot of pain compression thresholds in a rat model of inflammatory pain using three different doses of zoledronic acid. Measurements were taken at baseline (BL) and at various time points after dosing on the days indicated.

Bisphosphonate compounds such as pamidronate or pamidronic acid, neridronate or neridronic acid, olpadronate or olpadronic acid, alendronate or alendronic acid, incadronate or incadronic acid, ibandronate or ibandronic acid, risedronate or risedronic acid, zoledronate or zoledronic acid, etidronate or etidronic acid, clodronate or clodronic acid, tiludronate or tiludronic acid, etc., may be used for a number of medical purposes, such as treatment of undesirable conditions or diseases, including pain relief. This may be accomplished in many instances by administration of oral dosage forms. Generally, an oral dosage form comprising a bisphosphonate such as zoledronic acid is administered orally to a mammal, such as a human being, at least once, to treat a disease or condition, or to relieve pain.

The term "treating" or "treatment" broadly includes any kind of treatment activity, including the diagnosis, cure, mitigation, or prevention of disease in man or other animals, or any activity that otherwise affects the structure or any function of the body of man or other animals.

An oral dosage form of a bisphosphonate such as zoledronic acid may be used to treat, or provide relief of, any type of pain including, but not limited to, inflammatory pain, arthritis pain, complex regional pain syndrome, lumbosacral pain, musculoskeletal pain, neuropathic pain, chronic pain, cancer-related pain, acute pain, postoperative pain, etc. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, the mammal being treated is not suffering from bone metastasis. In some embodiments, the mammal being treated is not suffering from cancer. In some embodiments, the mammal being treated is not suffering from osteoporosis.

For example, zoledronic acid or another bisphosphonate may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, zoledronic acid or another bisphosphonate may also be administered orally to relieve neuropathic pain, including diabetic peripheral neuropathy, post-herpetic neuralgia, trigeminal neuralgia, monoradiculopathies, phantom limb pain, and central pain. Other causes of neuropathic pain include cancer-related pain, lumbar nerve root compression, spinal cord injury, post-stroke pain, central multiple sclerosis pain, HIV-associated neuropathy, and radio-therapy or chemo-therapy associated neuropathy. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, zoledronic acid or another bisphosphonate may be administered orally to relieve inflammatory pain including musculoskeletal pain, arthritis pain, and complex regional pain syndrome. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

Examples of musculoskeletal pain include low back pain; and pain associated with vertebral crush fractures, fibrous dysplasia, osteogenesis imperfecta, Paget's disease of bone, transient osteoporosis, and transient osteoporosis of the hip.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropaties including Charcot's foot, axial spondyloarthritis including ankylosing spondylitis, and SAPHO syndrome.

In some embodiments, a human being that is treated for arthritis by an oral dosage form of zoledronic acid has an age of about 10 years to about 90 years, about 20 years to about 80 years, about 30 years to about 75 years old, about 40 years to about 70 years, about 1 year to about 16 years, or about 80 years to about 95 years.

In some embodiments, a human being that is treated for arthritis by an oral dosage form of zoledronic acid has suffered from the arthritis for at least 1 month, at least 2 months, at least 6 months, or at least 1 year.

In some embodiments, the arthritis affects, a knee, an elbow, a wrist, a shoulder, or a hip.

In some embodiments, zoledronic acid or another bisphosphonate may be administered orally to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component.

Complex regional pain syndrome is a debilitating pain syndrome. It is characterized by severe pain in a limb accompanied by edema, and autonomic, motor and sensory changes.

With respect to use of oral zoledronic acid for relieving pain associated with an inflammatory condition, relief of pain can be short-term, e.g. for a period of hours after administration of the dosage form, and/or relief of pain can be long-term, e.g. lasting for days, weeks, or even months after oral administration of zoledronic acid. In some embodiments, a mammal, such as a human being, experiences significant pain relief at least about 3 hours, at least about 6 hours, at least about 12 hours, at least about 24 hours, at least about 48 hours, at least about one week, at least about 2 weeks, or at least about 3 weeks after administration of an oral dosage form comprising zoledronic acid. In some embodiments, a mammal, such as a human being, experiences significant pain relief during at least part of the time from about 3 hours to about 2 weeks, about 3 hours to about 3 weeks, about 3 hours to about 24 hours, about 6 hours to about 2 weeks, or about 6 hours to about 24 hours, about 3 days to about 2 weeks, about 6 days to about 2 weeks, after administration of an oral dosage form comprising zoledronic acid.

With respect to the treatment of any condition recited herein, in some embodiments a first oral dosage form comprising zoledronic acid is administered and a second oral dosage form comprising oral zoledronic acid is administered. The timing of the administration of the two dosage forms may be such that, with respect to the first oral dosage form, the second oral dosage with respect to the first oral dosage form, the second oral dosage form is administered at $5 \times T_{max}$ or greater (e.g., if $T_{max}$ is 1 hour, at 5 hours or later), at least $10 \times T_{max}$ or greater, at least about $15 \times T_{max}$ or greater, at least about $20 \times T_{max}$ or greater, at least about $50 \times T_{max}$ or greater, or at least about $200 \times T_{max}$ or greater, wherein $T_{max}$ is the time of maximum plasma concentration for the first oral dosage form.

Some embodiments include treatment of a condition recited herein, such as inflammatory pain, arthritis, or complex regional pain syndrome, wherein the treatment comprises either: administering only one dosage form to a mammal to treat the condition, or administering a first dosage form to the mammal, followed by administering a second dosage form to the mammal. If two or more dosage forms are administered, the second oral dosage form is administered before the maximum pain relieving effect of the first oral dosage form is achieved, or before a peak in the pain relieving effect of the first oral dosage form is experienced by a mammal, receiving the dosage form. In some embodiments, the second oral dosage form is administered before an observable pain relieving effect is achieved. In some embodiments, the second dosage form is administered about 12 hours to about 60 days, about 24 hours to about 28 days, about 24 hours to about 7 days, about 24 hours to about 14 days, or about 24 hours to about 21 days, after the first dosage form is administered.

Some embodiments include treatment of a condition recited herein, such as inflammatory pain, arthritis, or complex regional pain syndrome, wherein the treatment comprises administering a first dosage form to the mammal, followed by administering a second dosage form to the mammal, wherein the second dosage form is administered after the maximum pain relieving effect of the first oral dosage form is achieved, and the second oral dosage form is administered while the mammal is still experiencing pain relief from the first oral dosage form, or while the pain relieving effect from the first oral dosage form is observable. In some embodiments, the second dosage form is administered about 12 hours to about 60 days, about 24 hours to about 28 days, about 24 hours to about 7 days, about 24 hours to about 14 days, or about 24 hours to about 21 days, after the first dosage form is administered.

Zoledronic acid or another bisphosphonate may also be administered orally to relieve cancer-related pain, including pain associated with multiple myeloma and bone metastases from solid tumors. In some embodiments, zoledronic acid is used to treat pain that is not cancer-related pain. For example, zoledronic acid may be used to treat pain that is not associated with multiple myeloma, bone metastasis from solid tumors, hypercalcemia of malignancy, giant cell tumor of bone, blood cancers or leukemias, or solid tumors or cancers. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In addition to relieving pain, oral administration of zoledronic acid or another bisphosphonate may also be useful to treat diseases or conditions that may or may not include a pain component. For example, zoledronic acid or another bisphosphonate may be useful to treat any of the pain conditions or types of conditions listed above, including treatment that does not simply relieve the pain of those conditions, and treatment that is carried out in such a way that the condition is treated without pain relief occurring. In addition to any pain relief zoledronic acid or another bisphosphonate may or may not provide, zoledronic acid or another bisphosphonates may be used to treat a disease or condition such as a metabolic disease or condition; an inflammatory disease or condition, including an inflammatory disease or condition that is not associated with pain; a cancer disease or condition; a neurological disease or condition; etc. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, oral administration of zoledronic acid or another bisphosphonate may also be useful to treat complex regional pain syndrome, rheumatoid arthritis, osteoarthritis, erosive osteoarthritis, axial spondyloarthritis including ankylosing spondylitis, acute vertebral crush fracture, fibrous dysplasia, SAPHO syndrome, osteoporosis, transient osteoporosis, or transient osteoporosis of the hip. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

In some embodiments, oral administration of zoledronic acid or another bisphosphonate may also be useful to treat hypercalcemia of malignancy, multiple myeloma, bone metastases from solid tumors, Paget's disease of bone, giant cell tumor of bone, blood cancers or leukemias, or solid tumors or cancers. In some embodiments, enhanced bioavailability of the zoledronic acid may be achieved in treating one of these conditions by administering a dosage form comprising zoledronic acid in the form of a disodium salt. This may allow a reduced molar amount of the disodium salt to be used as compared to what would be used with the diacid form.

Zoledronic acid has the structure shown below, and is also referred to as zoledronate.

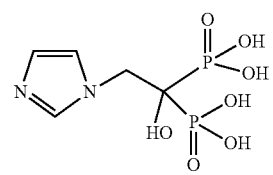

Zoledronic acid

Unless otherwise indicated, any reference to a compound herein, such as zoledronic acid, by structure, name, or any other means, includes pharmaceutically acceptable salts, such as the disodium salt; alternate solid forms, such as polymorphs, solvates, hydrates, etc.; tautomers; or any other chemical species that may rapidly convert to a compound described herein under conditions in which the compounds are used as described herein.

In some embodiments, zoledronic acid is administered in a dosage form comprising a salt form, such as a salt of a dianion of zoledronic acid. In some embodiments, zoledronic acid is administered in a dosage form comprising a disodium salt form of zoledronic acid. In some embodiments, zoledronic acid is administered in a sodium salt form, such as a monosodium salt, a disodium salt, a trisodium salt, etc. In some circumstances, use of the disodium salt may be desirable. For example, the disodium salt is much more soluble in water than the diacid form. As a result, in some processes, the disodium salt can be easier to work with than the diacid form. Additionally, the sodium salt may be more bioavailable and/or more rapidly absorbed when taken orally as compared to the diacid form.

The oral bioavailability of zoledronic acid may be enhanced by orally administering the zoledronic acid in the disodium salt form. For example, the bioavailability of zoledronic acid may be improved by at least about 10%, at least about 20%, at least about 30%, at least about 50%, and/or up to about 100%, or up to about 200%, as compared to administration of zoledronic acid in the diacid form.

Because of the improved bioavailability of the disodium salt a dosage form may contain, or a mammal, such as a human being, may receive, on a molar basis, less of the disodium salt form of zoledronic acid than would otherwise be administered of the diacid form of zoledronic acid. For example, a dosage form may contain, or a mammal may receive, at least about 10 mole % less, at least about 20 mole % less, at least about 40 mole % less, at least about 50 mole % less, and/or up to about 90 mole % less or 95 mole % less, of the disodium salt form as compared the amount of the diacid form of zoledronic acid that would otherwise be administered, such as a molar amount that would be administered of zoledronic acid in the diacid form in order to achieve the same plasma levels of zoledronic acid.

In some embodiments, a dosage form contains, or a mammal (such as a human being) is administered, an amount of the disodium salt form, on a molar basis, that has a value of about $0.8\, n_d$ to about $1.2\, n_d$ or about $0.9\, n_d$ to about $1.1\, n_d$, wherein:

$$n_d = (b_a/b_d)(n_a)$$

wherein $b_a$ is the bioavailability of the diacid form, $b_d$ is the bioavailability of the disodium salt form, and $n_a$ is the number of moles of the diacid that would be administered in a dosage form containing the diacid form of zoledronic acid. For example, if the diacid form has a bioavailability ($b_a$) of 0.01 and the disodium salt form has a bioavailabity ($b_d$) of 0.015, and a dosage form would normally contain 0.001 moles of the diacid, $n_d$ would be (0.01/0.015)(0.001 moles), or about 0.00067 moles. In some embodiments, the disodium salt is administered in an amount that has a value of about $n_d$.

With respect to oral dosage forms comprising a reduced molar amount of the disodium salt of zoledronic acid as compared to the diacid form of zoledronic acid, in some embodiments, the bioavailability of the zoledronic acid in the disodium salt form is sufficiently high that, if the drug is administered to a mammal, at least as much zoledronic acid is present in the blood of the mammal as would be present if zoledronic acid were administered in the diacid form.

With respect to oral dosage forms comprising the disodium salt form of zoledronic acid, in some embodiments, the disodium salt form is present in a lower molar amount than would be present if the zoledronic acid were in the diacid form; and the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

In some embodiments, the zoledronic acid in the disodium salt form is present in an amount such that the oral dosage form provides an area under the plasma concentration curve of zoledronic acid of about 4 ng·h/mL to about 2000 ng·h/mL to the mammal each time the zoledronic acid in the disodium salt is administered.

In some embodiments, the zoledronic acid in the disodium salt form is present in an amount such that the oral dosage form provides an area under the plasma concentration curve of zoledronic acid of about 100 ng·h/mL to about 2000 ng·h/mL, about 100 ng·h/mL to about 1000 ng·h/mL, about 500 ng·h/mL to about 1000 ng·h/mL, or about 500 ng·h/mL to about 700 ng·h/mL in the mammal to which the dosage form is administered. This amount may be suitable for administration of the oral dosage form about every 3 to 4 weeks.

In some embodiments, the zoledronic acid in the disodium salt form is present in an amount such that the oral dosage form provides an area under the plasma concentration curve of zoledronic acid of about 20 ng·h/mL to about 700 ng·h/mL, about 50 ng·h/mL to about 500 ng·h/mL, or about 100 ng·h/mL to about 200 ng·h/mL, in the mammal to which the dosage form is administered. This amount may be suitable for weekly administration of the oral dosage, or for administration of 3 to 5 individual dosages during a month. The individual dosages could be given at regular intervals, given during the first week, or at any other schedule that provides 3 to 5 dosages during the month.

In some embodiments, the zoledronic acid in the disodium salt form is present in an amount such that the oral dosage form provides an area under the plasma concentration curve of zoledronic acid of about 4 ng·h/mL to about 100 ng·h/mL, about 10 ng·h/mL to about 50 ng·h/mL, or about 10 ng·h/mL to about 30 ng·h/mL, in the mammal to which the dosage form is administered. This amount may be suitable for daily administration of the oral dosage form.

Oral administration of zoledronic acid, particularly oral administration of the disodium salt form of zoledronic acid, can result in more sustained plasma levels of the drug as compared to parenteral modes of administration, such intravenous or subcutaneous. For example, the amount of zoledronic acid in the plasma can be significantly higher for oral administration of the disodium salt about 24 hours or 48 hours, or longer, after administration. In some embodiments, oral zoledronic acid has a 24 hour sustained plasma level factor of about 1 or higher, such as about 1 to about 10, about 1 to about 5, about 3 to about 5, or about 3 to about 4. In some embodiments, an orally administered dosage form of zoledronic acid has a 24 hour sustained plasma level factor or a 48 hour sustained plasma level factor that is higher, such as at least 1.2 times, at least about 2 times, at least about 5 times, about 1.2 times to about 20 times, about 2 times to about 15 times, about 5 times to about 10 times, or about 8 to about 15 times that of intravenously administered zoledronic acid. A "sustained plasma level factor," $p_f$, is determined by the equation:

$$p_f = 1000(C_t/C_{max})$$

wherein $C_{max}$ is the maximum plasma concentration of zoledronic acid after it is administered and $C_t$ is the plasma concentration of zoledronic acid at the time of interest, such as 24 hours. For parenteral administration, the $C_{max}$ can be about the $C_0$, or the concentration right after injection of the entire amount of the drug into the body. Sustained plasma level factors can also be obtained for other times, such as 48 hours, by using the plasma concentration of zoledronic acid for $C_t$ in the equation above. For example, if the maximum plasma level of zoledronic acid after administration is 1000 ng/mL and the plasma level of zoledronic acid at 24 hours is 1 ng/mL, the 24 hour sustained plasma level factor is 1.

In some embodiments, the disodium salt form of zoledronic acid provides an enhancement to bioavailability, as compared to the diacid form of zoledronic acid, which adds to any enhancement to bioavailability provided by any bioavailability-enhancing agents in the dosage form. In some embodiments, the disodium salt form of zoledronic acid provides an enhancement to bioavailability, as compared to the diacid form of zoledronic acid, which is greater than any enhancement to bioavailability provided by any bioavailability-enhancing agents in the dosage form. In some embodiments, the disodium salt form of zoledronic acid may be administered in a dosage form that is substantially free of bioavailability-enhancing agents.

In some embodiments, a dosage form comprising a disodium salt of zoledronic acid is a solid.

In some embodiments, a dosage form comprising a disodium salt of zoledronic acid is used to treat an inflammatory condition.

In some embodiments, a dosage form comprising a disodium salt of zoledronic acid is used to treat arthritis.

In some embodiments, a dosage form comprising a disodium salt of zoledronic acid is used to treat complex regional pain syndrome.

In some embodiments, zoledronic acid is in a form that has an aqueous solubility, meaning the solubility in water, greater than 1% (w/v), about 5% (w/v) to about 50% (w/v), about 5% (w/v) to about 20% (w/v), about 10% (w/v) to about 15% (w/v), or about 12% (w/v) to about 13% (w/v).

The disodium salt form of zoledronic acid can be more compressible than the diacid form of zoledronic acid. This can make it easier for a dosage form to have a desired hardness. It can also make it easier to increase the drug load, so that a smaller tablet can be given for a given dosage strength. In some embodiments, a solid dosage form of zoledronic acid, such as the diacid form of zoledronic acid or the disodium salt form of zoledronic acid, can have a hardness of about 5 kPa to about 20 kPa or about 5 kPa to about 14 kPa.

Zoledronic acid or another bisphosphonate may be combined with a pharmaceutical carrier selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

Zoledronic acid or another bisphosphonate may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Zoledronic acid or another bisphosphonate may be administered to a human patient in a variety of forms adapted to the chosen route of administration, e.g., orally, rectally, or parenterally. Parenteral administration in this respect includes, but is not limited to, administration by the following routes: pulmonary, intrathecal, intravenous, intramuscular, subcutaneous, intraocular, intrasynovial, transepithelial including transdermal, sublingual and buccal; topically; nasal inhalation via insufflation; and rectal systemic.

The effective amount of zoledronic acid or another bisphosphonate will vary depending on various factors known to the treating physicians, such as the severity of the condition to be treated, route of administration, formulation and dosage forms, physical characteristics of the bisphosphonate compound used, and age, weight and response of the individual patients.

The amount of zoledronic acid or another bisphosphonate in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of zoledronic acid.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 75% (w/w), about 70% (w/w) to about 80% (w/w), or about 80% (w/w) to about 90% (w/w) of zoledronic acid.

Any suitable amount of zoledronic acid may be used. Some solid or liquid oral dosage forms, or units of oral dosage forms (referred to collectively herein as "oral dosage form(s)") may contain about 0.005 mg to about 20 mg, about 0.1 mg to about 10 mg, about 0.5 mg to about 10 mg, about 0.2 mg to about 5 mg, about 1 mg to about 500 mg, about 1 mg to about 50 mg, about 10 mg to about 250 mg, about 100 mg to about 300 mg, about 20 mg to about 200 mg, about 20 mg to about 150 mg, about 30 mg to about 100 mg, about 1 mg to about 1,000 mg, about 10 mg to about 50 mg, about 10 mg to about 300 mg, about 10 mg to about 150 mg, about 10 mg to about 100 mg, about 40 mg to about 150 mg, about 10 mg to about 600 mg, about 40 mg to about 600 mg, about 40 mg to about 2000 mg, about 40 mg to about 800 mg, about 25 mg to about 800 mg, about 30 mg to about 800 mg, about 10 mg to about 500 mg, about 50 mg to about 150 mg, about 50 mg to about 100 mg, about 50 mg to about 500 mg, about 100 mg to about 2000 mg, about 300 mg to about 1500 mg, about 200 mg to about 1000 mg, about 100 mg to about 500 mg, or about 150 mg of zoledronic acid, or any amount of zoledronic in a range bounded by, or between, any of these values. In some embodiments, the oral zoledronic acid is administered daily, weekly, monthly, every two or three months, once a year, or twice a year.

In some embodiments, an oral dosage form may contain about 10 mg/m$^2$ to about 20 mg/m$^2$, about 15 mg/m$^2$ to about 20 mg/m$^2$, about 18 mg/m$^2$, about 80 mg/m$^2$ to about 150 mg/m$^2$, about 90 mg/m$^2$ to about 150 mg/m$^2$, about 100 mg/m$^2$ to about 150 mg/m$^2$ of zoledronic acid, or any amount of zoledronic in a range bounded by, or between, any of these values. All dosage ranges or amounts expressed in mg/m$^2$ are based upon the body surface area of the mammal.

In some embodiments the daily oral dose of zoledronic acid is about 0.005 mg to about 20 mg, about 0.1 mg to about 10 mg, about 0.5 mg to about 10 mg, about 0.2 mg to about 5 mg, or any amount of zoledronic acid in a range bounded by, or between, any of these values. In some embodiments, the daily or dose of zoledronic acid is less than about 35 mg/m$^2$, less than about 30 mg/m$^2$, less than about 25 mg/m$^2$, about 1 mg/m$^2$ to about 35 mg/m$^2$, about 1 mg/m$^2$ to about 30 mg/m$^2$, about 1.5 mg/m$^2$ to about 25 mg/m$^2$, about 1.8 mg/m$^2$ to about 20 mg/m$^2$, about 10 mg/m$^4$ to about 20 mg/m$^2$, about 10 mg/m$^2$ to about 30 mg/m$^2$, about 15 mg/m$^2$ to about 20 mg/m$^2$, about 18 mg/m$^2$, or any amount of zoledronic acid in a range bounded by, or between, any of these values.

In some embodiments the weekly oral dose of zoledronic add is about 1 mg to about 1000 mg, about 1 mg to about 500 mg, about 10 mg to about 250 mg, about 100 mg to about 300 mg, about 10 mg to about 100 mg, about 10 mg to about 150 mg, about 10 mg to about 100 mg, about 10 mg to about 300 mg, about 20 mg to about 150 mg, or about 30 mg to about 100 mg. In some embodiments, the weeky oral dose of zoledronic acid is less than about 250 mg/m$^2$, less than about 200 mg/m$^2$, less than about 175 mg/m$^2$, about 6 mg/m$^2$ to about 250 mg/m$^2$, about 10 mg/m$^2$ to about 210 mg/m$^4$, about 10 mg/m$^2$ to about 170 mg/m$^2$, about 4 mg/m$^2$ to about 140 mg/m$^2$, about 100 mg/m$^2$ to about 140 mg/m$^2$, about 126 mg/m$^2$, or any amount of zoledronic acid in a range bounded by, or between, any of these values. The weekly oral dose may be given as a single dose, given once during the week, or may be given in 2, 3, 4, 5, 6, or 7 individual doses during the week.

In some embodiments, the monthly dose of zoledronic acid, or the amount of zoledronic acid that is administered over a period of a month, is about 5000 mg or less, about 4000 mg or less, about 3000 mg or less, about 2000 mg or less, about 1000 mg or less, about 700 mg or less, about 600 mg or less, about 1 mg to about 4,000 mg, about 1 mg to about 1,000 mg, about 10 mg to about 1000 mg, about 50 mg to about 1000 mg, about 10 mg to about 600 mg, about 40 mg to about 600 mg, about 50 mg to about 600 mg, or about 100 mg to about 600 mg, about 40 mg to about 2000 mg, about 40 mg to about 800 mg, about 50 mg to about 800 mg, or about 100 mg to about 800 mg, about 40 mg to about 1000 mg, about 50 mg to about 1000 mg, or about 100 mg to about 1000 mg, or any monthly dose in a range bounded by, or between, any of these values. In some embodiments, the monthly oral dose of zoledronic acid is less than about 1000 mg/m$^2$, less than about 800 mg/m$^2$, less than about 600 mg/m$^2$, about 10 mg/m$^2$ to about 1000 mg/m$^2$, about 50 mg/m$^2$ to about 800 mg/m$^2$, about 70 mg/m$^2$ to about 700 mg/m$^2$, about 100 mg/m$^2$ to about 700 mg/m$^2$, about 100 mg/m$^2$ to about 600 mg/m$^2$, about 50 mg/m$^2$ to about 200 mg/m$^2$, about 300 mg/m$^2$ to about 600 mg/m$^2$, about 450 mg/m$^2$ to about 600 mg/m$^2$, about 300 mg/m$^2$ to about 1000 mg/m$^2$, about 400 mg/m$^2$ to about 1000 mg/m$^2$, about 500 mg/m$^2$ to about 1000 mg/m$^2$, about 400 mg/m$^2$ to about 700 mg/m$^2$, about 500 mg/m$^2$ to about 600 mg/m$^2$, about 540 mg/m$^2$, or any amount of zoledronic acid in a range bounded by, or between, any of these values. A monthly dose may be given as a single dose, or as two or more individual doses administered during the month. In some embodiments, the monthly dose is administered in 2 or 3 weekly doses. In some embodiments, the monthly dose is administered in 4 or 5 weekly doses. In some embodiments, the monthly dose is administered in 28 to 31 daily doses. In some embodiments, the monthly dose is administered in 5 to 10 individual doses during the month. The monthly dose may be administered for only 1 month, or may be repeatedly administered for 2 or more months.

The oral zoledronic acid, or disodium salt thereof, may be administered in combination with about 0.1 mg to about 10 mg of zoledronic acid, or a salt thereof, administered parenterally, such as intravenously. In some embodiments, about 50 mg, about 100 mg, or about 150 mg of the disodium salt of zoledronic acid is administered orally in combination with 1 mg parenteral, such as intravenous, zoledronic acid. In some embodiments the parenteral dose of zoledronic acid is about 0.25 mg to about 25 mg, about 0.25 mg to about 10 mg, or about 0.5 mg to about 7.5 mg.

With respect to oral administration of zoledronic acid, or another bisphosphonate, for the treatment of pain associated with inflammation, arthritis, CRPS, or any other condition recited herein, it may helpful if the mammal or human being to which the zoledronic acid is administered does not eat food or drink beverage, (other than any water required to swallow the oral dosage form) for at least about 1 hour, at least about 2 hours, at least about 4 hours, at least about 6 hours, at least about 8 hours, at least about 10 hours, or at least about 12 hours before the zoledronic acid is administered. It may also be helpful if the mammal or human being to which the zoledronic acid is administered does not eat food or drink beverage for at least about 30 minutes, at least about 1 hour, at least about 2 hours, at least about 3 hours, or at least about 4 hours after the zoledronic acid is administered. In some embodiments, a human being to which the zoledronic acid is administered avoids lying down, or remains upright or sits upright, for at least about 30 minutes or about 1 hour after receiving a dosage form containing zoledronic acid. Avoiding food or beverage before or after oral administration of zoledronic acid can improve the bioavailability of the zoledronic acid.

The oral bioavailability of zoledronic acid in a dosage form can vary. Some dosage forms may have ingredients added to enhance the bioavailability. However, bioavailability enhancement is not necessary for an oral dosage form to be effective. In some embodiments, the dosage form is substantially free of bioavailability-enhancing agents. In some embodiments, an oral dosage form may have an oral bioavailability of zoledronic acid of about 0.01% to about 10%, about 0.1% to about 7%, about 0.1% to about 5%, etc. Without ingredients or other methods to enhance bioavailability, zoledronic acid typically has a low bioavailability in an oral dosage form. In some embodiments, the oral bioavailability of zoledronic acid is unenhanced or substantially unenhanced. For example, the oral bioavailability of zoledronic acid can be about 0.01% to about 5%, about 0.01% to about 4%, about 0.1% to about 3%, about 0.1% to about 2%, about 0.2% to about 2%, about 0.2% to about 1.5%, about 0.3% to about 1.5%, about 0.3% to about 1%, about 0.1% to about 0.5%, about 0.3% to about 0.5%, about 0.5% to about 1%, about 0.6% to about 0.7%, about 0.7% to about 0.8%, about 0.8% to about 0.9%, about 0.9%, about 1% to about 1.1%, about 1.1% to about 1.2%, about 1.2% to about 1.3%, about 1.3% to about 1.4%, about 1.4% to about 1.5%, about 1.5% to about 1.6%, about 1.6% to about 1.8%, or about 1.8% to about 2%.

One embodiment is a pharmaceutical composition comprising zoledronic acid wherein the oral bioavailability of zoledronic acid in the dosage form is from about 0.01% to about 10%.

In some embodiments, the oral bioavailability of zoledronic acid in the dosage form is about 0.01% to about 5%.

In some embodiments, the oral bioavailability of zoledronic add in the dosage form is about 0.1% to about 7%.

In some embodiments, the oral bioavailability of zoledronic acid in the dosage form is about 0.1% to about 5%.

In some embodiments, the oral bioavailability of zoledronic acid in the dosage form is about 0.1% to about 3%.

In some embodiments, the oral bioavailability of zoledronic add in the dosage form is about 0.1% to about 2%.

In some embodiments, the oral bioavailability of zoledronic acid in the dosage form is about 0.2% to about 2%.

In some embodiments, the oral bioavailability of zoledronic acid in the dosage form is about 0.2% to about 1.5%.

In some embodiments, the oral bioavailability of zoledronic add in the dosage form is about 0.3% to about 1.5%.

In some embodiments, the or bioavailability of zoledronic add in the dosage form is about 0.3% to about 1.0%.

In some embodiments, an oral dosage form comprises about 10 mg to about 300 mg of zoledronic acid, and is administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, and is administered daily for about 2 to about 15 consecutive days. This regimen may be repeated once monthly, once every two months, once every three months, once every four months, once every five months, once every six months, once yearly, or once every two years.

In some embodiments, an oral dosage form comprises about 10 mg to about 150 mg or about 10 mg to about 100 mg of zoledronic acid, and is administered daily for about 5 to about 10 consecutive days. This regimen may be repeated once monthly, once every two months, once every three months, once every four months, once every five months, once every six months, once yearly, or once every two years.

In some embodiments, an oral dosage form comprises about 40 mg to about 150 mg of zoledronic acid, and is administered daily for about 5 to about 10 consecutive days. This regimen may be repeated once monthly, once every two months, once every three months, once every four months, once every five months, once every six months, once yearly, or once every two years.

In some embodiments, the oral zoledronic acid may be administered as one dose of about 100 mg to about 2000 mg. In some embodiments, the oral zoledronic acid may be administered as one dose of about 300 mg to about 1500 mg. In some embodiments, the oral zoledronic acid may be administered as one dose of about 200 mg to about 1000 mg. The dose of zoledronic acid may be administered in a single or divided dose.

Zoledronic acid may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

Some compositions or dosage forms may be a liquid, or may comprise a solid phase dispersed in a liquid.

Zoledronic acid may be formulated for parental or intraperitoneal administration. Solutions of the active compounds as free acids or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

In some embodiments, an oral dosage form may comprise a silicified microcrystalline cellulose such as Prosolv. For example, about 20% (wt/wt) to about 70% (wt/wt), about 10% (wt/wt) to about 20% (wt/wt), about 20% (wt/wt) to about 40% (wt/wt), about 25% (wt/wt) to about 30% (wt/wt), about 40% (wt/wt) to about 50% (wt/wt), or about 45% (wt/wt) to about 50% (wt/wt) silicified microcrystalline cellulose may be present in an oral dosage form or a unit of an oral dosage form.

In some embodiments, an oral dosage form may comprise a crosslinked polyvinylpyrrolidone such as crospovidone. For example, about 1% (wt/wt) to about 10% (wt/wt), about 1% (wt/wt) to about 5% (wt/wt), or about 1% (wt/wt) to about 3% (wt/wt) crosslinked polyvinylpyrrolidone may be present in an oral dosage form or a unit of an oral dosage form.

In some embodiments, an oral dosage form may comprise a fumed silica such as Aerosil. For example, about 0.1% (wt/wt) to about 10% (wt/wt), about 0.1% (wt/wt) to about 1% (wt/wt), or about 0.4% (wt/wt) to about 0.6% (wt/wt) fumed silica may be present in an oral dosage form or a unit of an oral dosage form.

In some embodiments, an oral dosage form may comprise magnesium stearate. For example, about 0.1% (wt/wt) to about 10% (wt/wt), about 0.1% (wt/wt) to about 1% (wt/wt), or about 0.4% (wt/wt) to about 0.6% (wt/wt) magnesium stearate may be present in an oral dosage form or a unit of an oral dosage form.

An oral dosage form comprising zoledronic acid or another bisphosphonate may be included in a pharmaceutical product comprising more than one unit of the oral dosage form.

A pharmaceutical product containing or dosage forms for daily use can contain 28, 29, 30, or 31 units of the oral dosage form for a monthly supply. An approximately 6 week daily supply can contain 40 to 45 units of the oral dosage form. An approximately 3 month daily supply can contain 85 to 95 units of the oral dosage form. An approximately six-month daily supply can contain 170 to 200 units of the oral dosage form. An approximately one year daily supply can contain 350 to 380 units of the oral dosage form.

A pharmaceutical product containing or dosage forms for weekly use can contain 4 or 5 units of the oral dosage form for a monthly supply. An approximately 2 month weekly supply can contain 8 or 9 units of the oral dosage form. An approximately 6 week weekly supply can contain about 6 units of the oral dosage form. An approximately 3 month weekly supply can contain 12, 13 or 14 units of the oral dosage form. An approximately six-month weekly supply can contain 22 to 30 units of the oral dosage form. An approximately one year weekly supply can contain 45 to 60 units of the oral dosage form.

A pharmaceutical product may accommodate other dosing regimes. For example, a pharmaceutical product may comprise 5 to 10 units of the oral dosage form, wherein each unit of the oral dosage form contains about 40 mg to about 150 mg of zoledronic acid. Some pharmaceutical products may comprise 1 to 10 units of the oral dosage form, wherein the product contains about 200 mg to about 2000 mg of zoledronic acid. For such a product, each unit of the oral dosage form may be taken daily for 1 to 10 days or 5 to 10 days during a month, such as at the beginning of a month.

Some oral dosage forms comprising zoledronic acid or a salt thereof may have enteric coatings or film coatings.

In the examples below, zoledronic acid was administered in the disodium salt form as disodium zoledronate tetrahydrate. No bioavailability enhancing agents were used in the test compositions.

Example 1

Effect of Orally Administered Zoledronic Acid in Rat Model of Inflammatory Pain

Method:

The effect of orally administered zoledronic acid on inflammatory pain was examined using the rat complete Freund's adjuvant (CFA) model. Inflammatory pain was induced by injection of 100% CFA in a 75 µL volume into the left hind paws of Sprague-Dawley rats on day 0, followed by assessments on days 1-3. Animals were orally administered vehicle (control), zoledronic acid 18 mg/m$^2$ (or 3 mg/kg), zoledronic acid 120 mg/m$^2$ (or 20 mg/kg), or zoledronic acid 900 mg/m$^2$ (or 150 mg/kg) daily on days 1-3. Drug was dissolved in distilled water and prepared fresh daily. Animals were fasted prior to dosing. Under current FDA guidelines for extrapolating starting dosages from animals to humans, dosages expressed in mg/m$^2$ are considered equivalent between mammalian species. Thus, for example, 18 mg/m$^2$ in a rat is considered equivalent to 18 mg/m$^2$ in a human being, while 3 mg/kg in a rat may not be equivalent to 3 mg/kg in a human being.

Values for inflammatory pain (mechanical hyperalgesia) in the vehicle and drug-treated animals were obtained on day 0 prior to CFA injection, and at baseline and post-treatment on days 1-3. Pain was assessed using a digital Randall-Selitto device (dRS; IITC Life Sciences, Woodland Hills, Calif.). Animals were placed in a restraint sling that suspended the animal, leaving the hind limbs available for testing. Paw compression threshold was measured by applying increasing pressure to the plantar surface of the hind paw with a dome-shaped tip placed between the 3rd and 4th metatarsus. Pressure was applied gradually over approximately 10 seconds. Measurements were taken from the first observed nocifensive behavior of vocalization, struggle or withdrawal. A cut-off value of 300 g was used to prevent injury to the animal.

Reversal of inflammatory pain was calculated according to the formula:

% reversal=(Post-treatment−Post-CFA baseline)/(Pre-CFA baseline−Post-CFA baseline)×100.

The experiment was carried out using 9-10 animals per group.

Results:

Oral administration of zoledronic acid significantly improved inflammatory pain thresholds compared to vehicle. Pain threshold measurements taken at various times are shown in FIG. 1. Paw compression thresholds in the 18 mg/m$^2$ group were higher than for vehicle during the entire measurement period after 30 minutes from the start of treatment. On day three, paw compression thresholds for both the 18 mg/m$^2$ and 900 mg/m$^2$ groups were greater than for vehicle. An improvement in pain threshold of 49% and 83% from baseline was observed for the 18 mg/m$^2$ and the 900 mg/m$^2$ groups respectively.

Orally administered zoledronic acid produced a 29% reversal of inflammatory pain at the 18 mg/m$^2$, and a 48% reversal at the 900 mg/m$^2$ dose. This magnitude of effect is comparable to that obtained with clinical doses of commercially available NSAIDs when tested in a similar model of inflammatory pain. Under current FDA guidelines, the reference body surface area of a human adult is 1.62 m$^2$. Thus, a daily dose of 18 mg/m$^2$ corresponds to a monthly dose of about 500-560 mg/m$^2$ or a human dose of about 800-900 mg.

Surprisingly, the two higher doses resulted in thresholds that were lower than vehicle on the first two days of dosing. The 120 mg/m$^2$ group was approximately equal or inferior to vehicle at all time points during the assessment period. While the 900 mg/m$^2$ group showed effectiveness on day 3, this result was accompanied by significant toxicity necessitating euthanization of all the animals in this group two days after cessation of dosing.

Example 2

Effect of Orally Administered Zoledronic Acid in Rat Model of Arthritis Pain Method The effect of orally administered zoledronic acid on arthritis pain was examined in the rat complete Freund's adjuvant (CFA) model of arthritis pain. In this model, injection of 100% complete Freund's adjuvant (CFA) in a 75 µL volume into the left hind paws is followed by a 10-14 day period to allow for the development of arthritis pain. Animals were orally administered vehicle (control), zoledronic acid 54 mg/m$^2$ (or 9 mg/kg), or zoledronic acid 360 mg/m$^2$ (or 60 mg/kg), divided in three equal daily doses on the first three days post CFA injection. Drug was dissolved in distilled water and prepared fresh daily. Animals were fasted prior to dosing.

Arthritis pain (mechanical hyperalgesia) in the vehicle and drug-treated animals was evaluated on day 14 post CFA injection using a digital Randall-Selitto device (dRS; IITC Life Sciences, Woodland Hills, Calif.). Animals were placed in a restraint sling that suspended the animal, leaving the hind limbs available for testing. Paw compression threshold was measured by applying increasing pressure to the plantar surface of the hind paw with a dome-shaped tip placed between the 3rd and 4th metatarsus. Pressure was applied gradually over approximately 10 seconds. Measurements were taken from the first observed nocifensive behavior of vocalization, struggle or withdrawal. A cut-off value of 300 g was used to prevent injury to the animal.

Reversal of arthritis pain in the ipsilateral (CFA-injected) paw was calculated according to the formula:

% reversal=(ipsilateral drug threshold−ipsilateral vehicle threshold)/(contralateral vehicle threshold−ipsilateral vehicle threshold)×100.

The experiment was carried out using 7-10 animals per group.

Figure 2A:
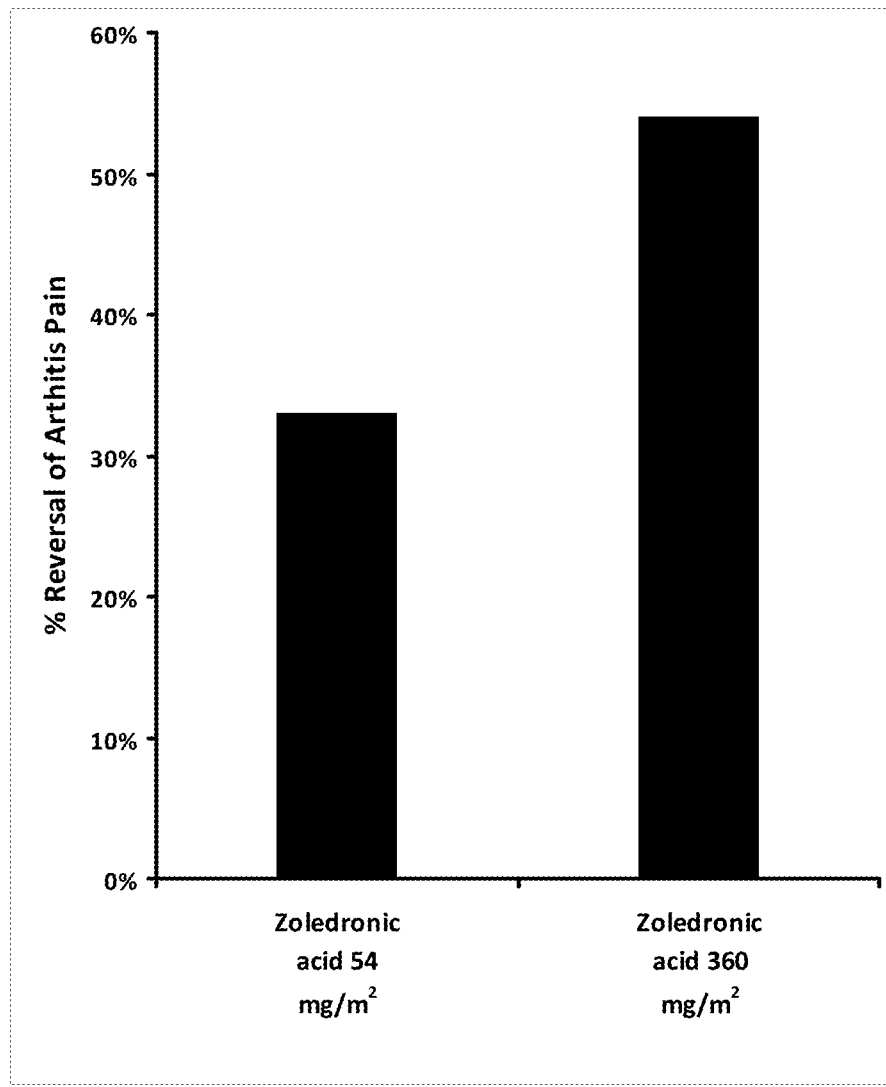
FIG. 2A is a graph depicting reversal of arthritis pain for two different doses of zoledronic acid in a rat model of arthritis pain.
Figure 2B:
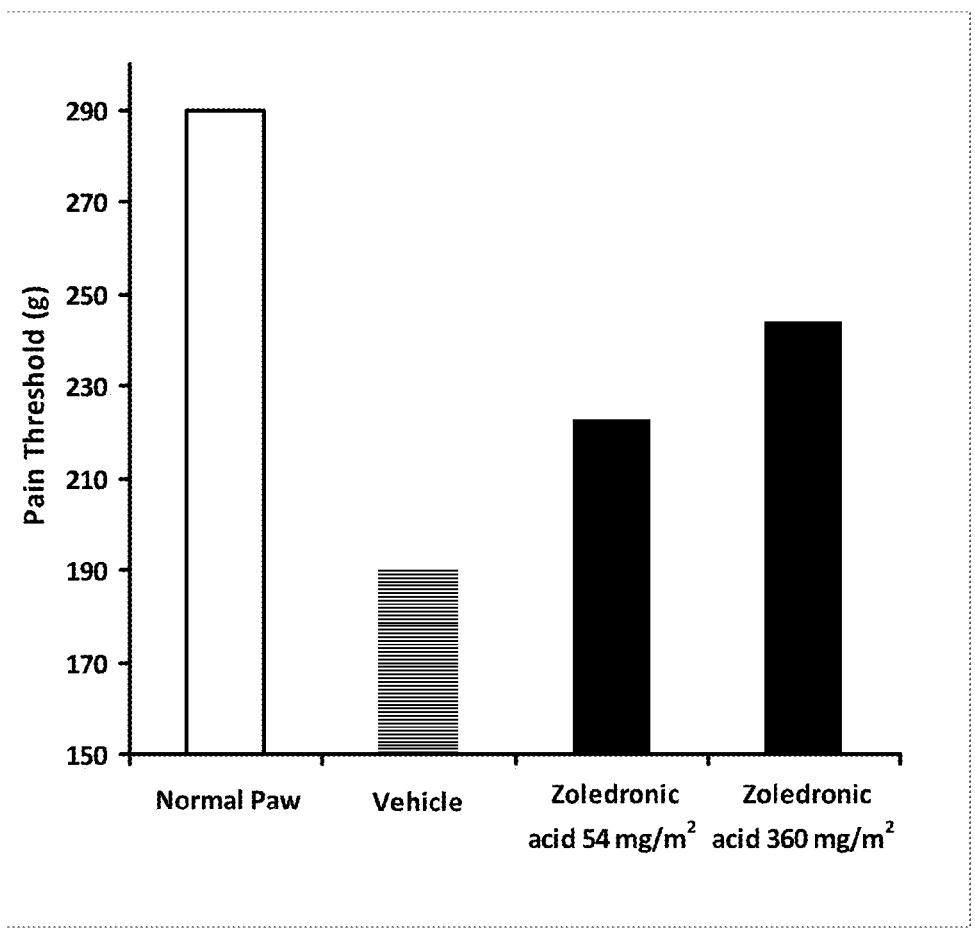
FIG. 2B is a graph depicting pain thresholds for two different doses of zoledronic acid in a rat model of arthritis pain.

Results:

Oral administration of zoledronic acid significantly improved arthritis pain thresholds compared to vehicle. As shown in FIGS. 2A and 2B, orally administered zoledronic acid produced a dose-dependent reversal of arthritis pain. A reversal of 33% was observed in the 54 mg/m$^2$ group, and reversal of 54% was observed in the 360 mg/m$^2$ group. Under current FDA guidelines, the reference body surface area of a human adult is 1.62 m$^2$. Thus, 54 mg/m$^2$ in a rat is equivalent to an implied human dose of about 87 mg, and 360 mg/m$^2$ in a rat is equivalent to an implied human dose of about 583 mg.

Example 3

Treatment of Complex Regional Pain Syndrome with Orally Administered Zoledronic Acid The effect of orally administered zoledronic acid was examined in the rat tibia fracture model of complex regional pain syndrome (CRPS). CRPS was induced in the rats by fracturing the right distal tibias of the animals and casting the fractured hindpaws for 4 weeks, as described in Guo T Z et al. (*Pain.* 2004; 108:95-107). This animal model has been shown to replicate the inciting trauma, natural history, signs, symptoms, and pathologic changes observed in human CRPS patients (Kingery W S et al., *Pain.* 2003; 104:75-84).

Animals were orally administered either vehicle (control) or zoledronic acid, in a dosage of 18 mg/m$^2$/day (3 mg/kg/day) for 28 days, starting on the day of fracture and casting. Drug was dissolved in distilled water and administered by gavage. Animals were fasted for 4 hours before and 2 hours after dosing. At the end of the 28-day period, casts were removed, and on the following day, the rats were tested for hindpaw pain, edema, and warmth.

Pain Assessments

Pain was assessed by measuring hyperalgesia, and weight bearing.

To measure hyperalgesia, an up-down von Frey testing paradigm was used. Rats were placed in a clear plastic cylinder (20 cm in diameter) with a wire mesh bottom and allowed to acclimate for 15 minutes. The paw was tested with one of a series of eight von Frey hairs ranging in stiffness from 0.41 g to 15.14 g. The von Frey hair was applied against the hindpaw plantar skin at approximately midsole, taking care to avoid the tori pads. The fiber was pushed until it slightly bowed and then it was jiggled in that position for 6 seconds. Stimuli were presented at an interval of several seconds. Hindpaw withdrawal from the fiber was considered a positive response. The initial fiber presentation was 2.1 g and the fibers were presented according to the up-down method of Dixon to generate six responses in the immediate vicinity of the 50% threshold. Stimuli were presented at an interval of several seconds.

An incapacitance device (IITC Inc. Life Science, Woodland, Calif., USA) was used to measure hindpaw weight bearing, a postural effect of pain. The rats were manually held in a vertical position over the apparatus with the hindpaws resting on separate metal scale plates and the entire weight of the rat was supported on the hindpaws. The duration of each measurement was 6 seconds and 10 consecutive measurements were taken at 60-second intervals. Eight readings (excluding the highest and lowest ones) were averaged to calculate the bilateral hindpaw weight-bearing values. Weight bearing data were analyzed as the ratio between right (fracture) and left hindpaw weight bearing values ((2R/(R+L))×100%).

Edema Assessment

A laser sensor technique was used to determine the dorsal-ventral thickness of the hindpaw. Before baseline testing the bilateral hindpaws were tattooed with a 2 to 3 mm spot on the dorsal skin over the midpoint of the third metatarsal. For laser measurements each rat was briefly anesthetized with isoflurane and then held vertically so the hindpaw rested on a table top below the laser. The paw was gently held flat on the table with a small metal rod applied to the top of the ankle joint. Using optical triangulation, a laser with a distance measuring sensor was used to determine the distance to the table top and to the top of the hindpaw at the tattoo site and the difference was used to calculate the dorsal-ventral paw thickness. The measurement sensor device used in these experiments (4381 Precicura, Limab, Goteborg, Sweden) has a measurement range of 200 mm with a 0.01 mm resolution.

Hindpaw Temperature Measurement

The temperature of the hindpaw was measured using a fine wire thermocouple (Omega, Stanford, Conn., USA) applied to the paw skin. Six sites were tested per hindpaw. The six measurements for each hindpaw were averaged for the mean temperature.

Results

Figure 3:
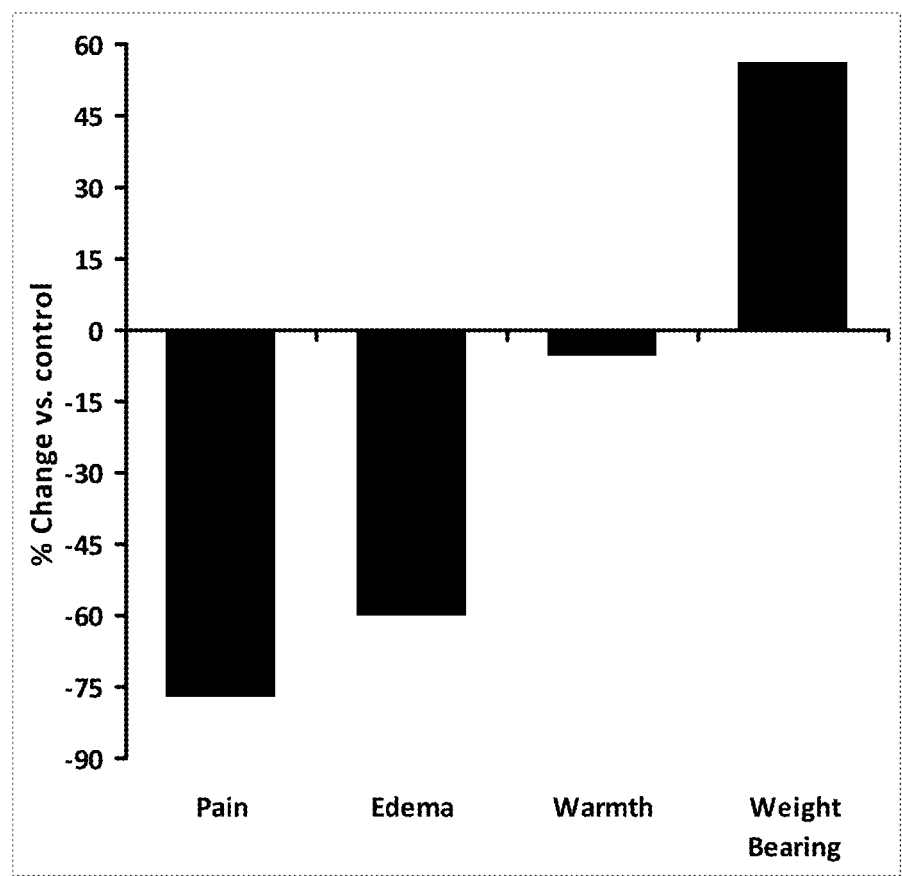
FIG. 3 is a graph summarizing the results for vehicle and zoledronic acid treated rats in a rat model of complex regional pain syndrome.

As illustrated in FIG. 3, treatment with orally administered zoledronic acid reversed pain, restored weight bearing, and prevented edema as compared to vehicle treated animals.

Figure 4:
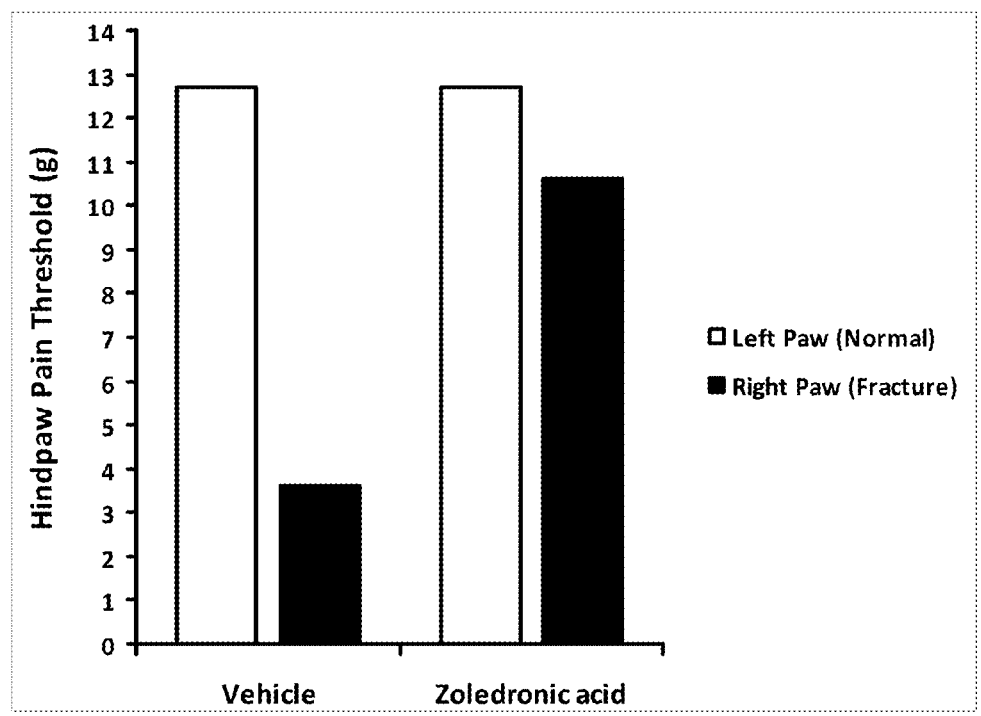
FIG. 4 depicts hindpaw pain thresholds for vehicle and zoledronic acid treated rats in a rat model of complex regional pain syndrome.

As illustrated in FIG. 4, von Frey pain thresholds for the right (fracture) hindpaw were reduced by 72% versus the contralateral (normal) hindpaw in vehicle treated animals. Zoledronate treatment reversed fracture induced pain by 77% as compared to vehicle treatment.

Figure 5:
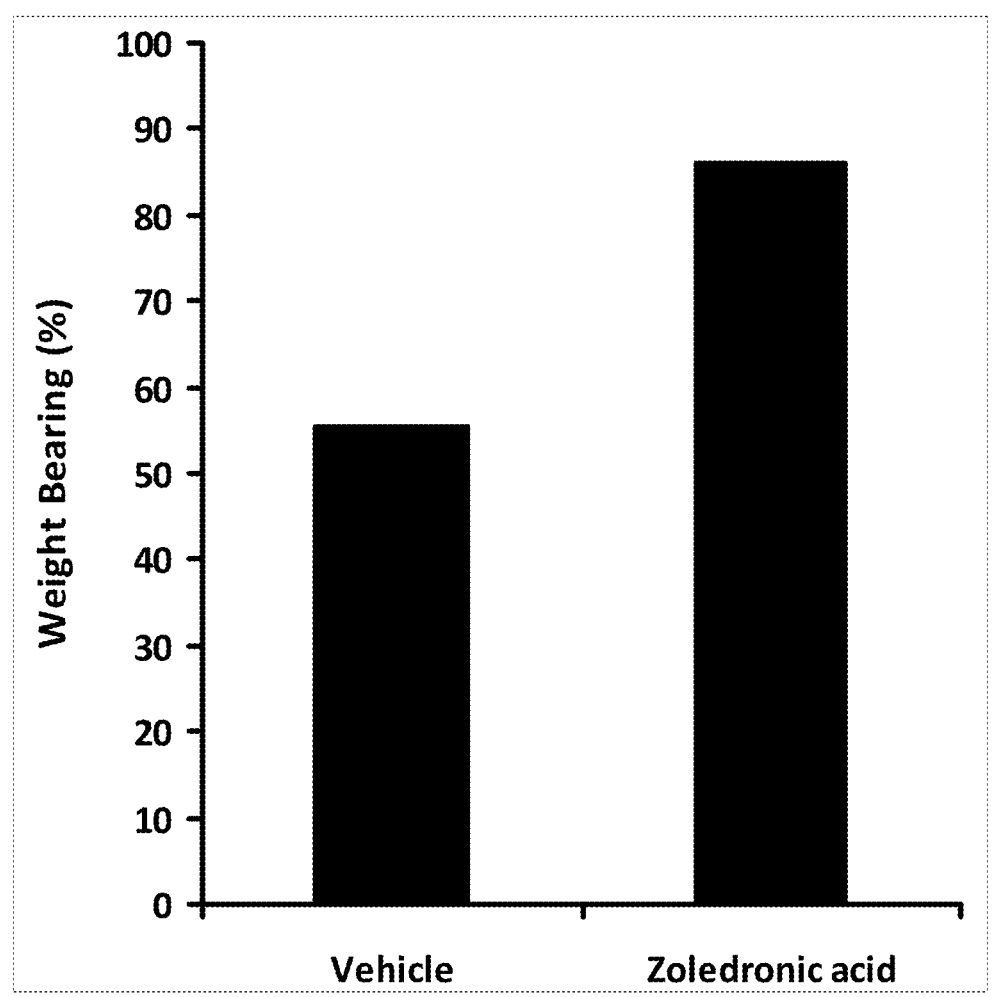
FIG. 5 depicts weight bearing for vehicle and zoledronic acid treated rats in a rat model of complex regional pain syndrome.

As illustrated in FIG. 5, reduction in weight bearing, a postural effect of pain, was significantly higher in the vehicle treated group as compared to the zoledronic acid treated group. Weight bearing on the fracture hindlimb was reduced to 55% of normal in the vehicle treated group. Zoledronate treatment significantly restored hindlimb weight bearing as compared to vehicle treatment (86% of normal).

Figure 6:
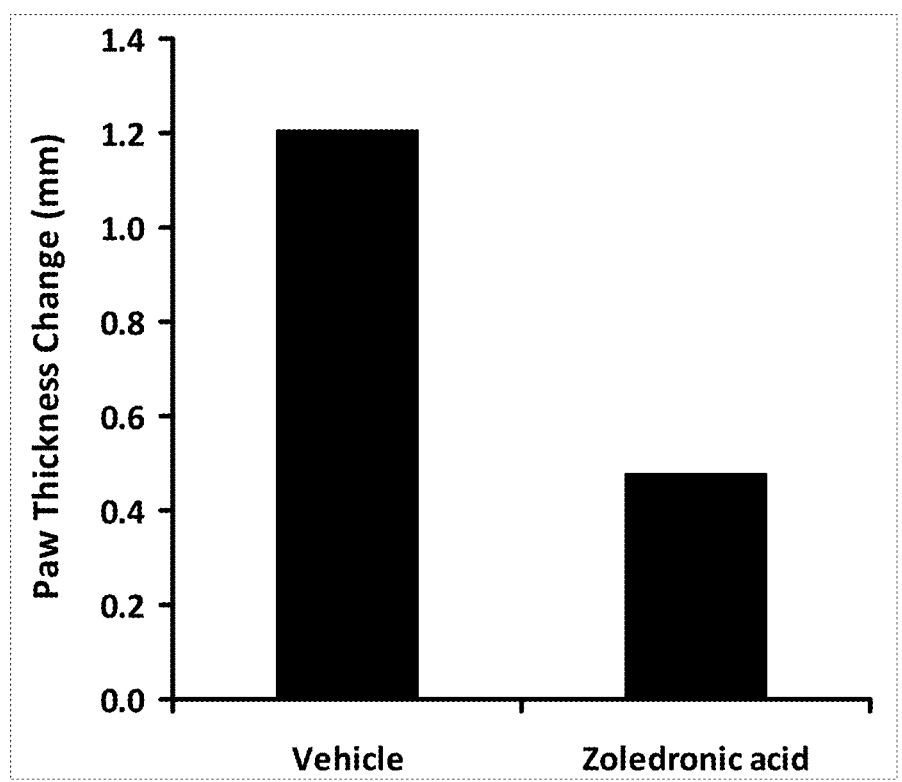
FIG. 6 depicts paw thickness change for vehicle and zoledronic acid treated rats in a rat model of complex regional pain syndrome.

As illustrated in FIG. 6, the expected increase in hindpaw thickness was greater in the vehicle treated group as compared to the zoledronic acid treated group, reflecting the development of edema. Zoledronate treatment reduced hindpaw edema by 60% versus vehicle treatment.

Zoledronic acid reduced hindpaw warmth by 5% versus vehicle treatment.

The daily dose in the above experiment was 18 mg/m$^2$/day. Under current FDA guidelines, the reference body surface area of a human adult is 1.62 m$^2$. Thus, a daily dose of 18 mg/m$^2$ corresponds to a monthly dose of about 500-560 mg/m$^2$ or a human dose of about 800-900 mg.

Example 6

Solubility of Disodium Salt of Zoledronic Acid

The aqueous solubility of zoledronic acid and disodium zoledronate tetrahydrate was determined. One gram of the test compound was measured in to a beaker. Demineralized water (pH 5.5) was then added in small increments to the test compound, and sonification was applied to the mixture. The procedure was continued until complete dissolution was achieved. Full dissolution was determined to have been reached when a clear solution was present with no visible material. The volume of water required to reach full dissolution was used to calculate a solubility value expressed in grams per 100 mL. The procedure was performed for each compound.

Results

Figure 7:
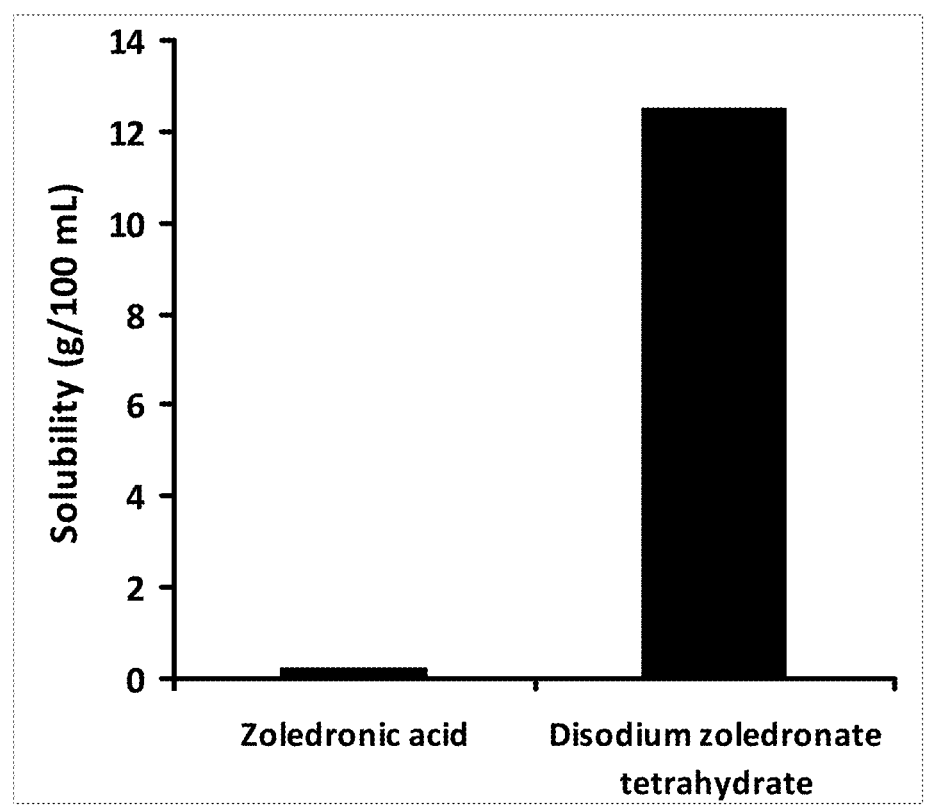
FIG. 7 depicts the aqueous solubility of disodium zoledronate tetrahydrate as compared to the diacid form of zoledronic acid.

As shown in FIG. 7, the aqueous solubility of disodium zoledronate tetrahydrate is approximately 50 times that of zoledronic acid. Disodium zoledronate tetrahydrate has a solubility of 12.5 g/100 mL compared to only 0.25 g/100 mL for zoledronic acid.

Example 7

Bioavailability of Orally Administered Zoledronic Acid and Disodium Zoledronate

Tablets were manufactured containing either pure zoledronic acid or the disodium salt of zoledronic acid (disodium zoledronate tetrahydrate). Both types of tablets contained 50 mg of zoledronic acid equivalent per tablet. Identical excipients were used in both types of tablets, with amounts adjusted to account for the difference in molecular weights between the acid and the disodium salt.

Beagle dogs were orally administered tablets containing 150 mg zoledronic acid equivalent either in the form of disodium zoledronate (Group 1) or pure zoledronic acid (Group 2). Each animal was given three 50 mg equivalent tablets (150 mg total), which were administered together. The animal's oral cavity was wetted with water before placing the tablets on the back of the animal's tongue. Animals were fasted before and after dosing. Animals were 6 to 9 months of age and weighed 6 to 10 kg on the day of dosing. There were three dogs per group.

Serial blood samples were collected from each animal by venipuncture of the jugular vein at various points after dosing for measurement of plasma concentrations of zoledronic acid. Blood samples were collected into chilled tubes containing $K_2EDTA$ as the anticoagulant. Samples were then centrifuged at approximately 3000 rpm at +4° C. for 10 minutes for plasma derivation. Plasma concentrations of zoledronic acid were measured using an LC/MS/MS method.

Results

Figure 8:
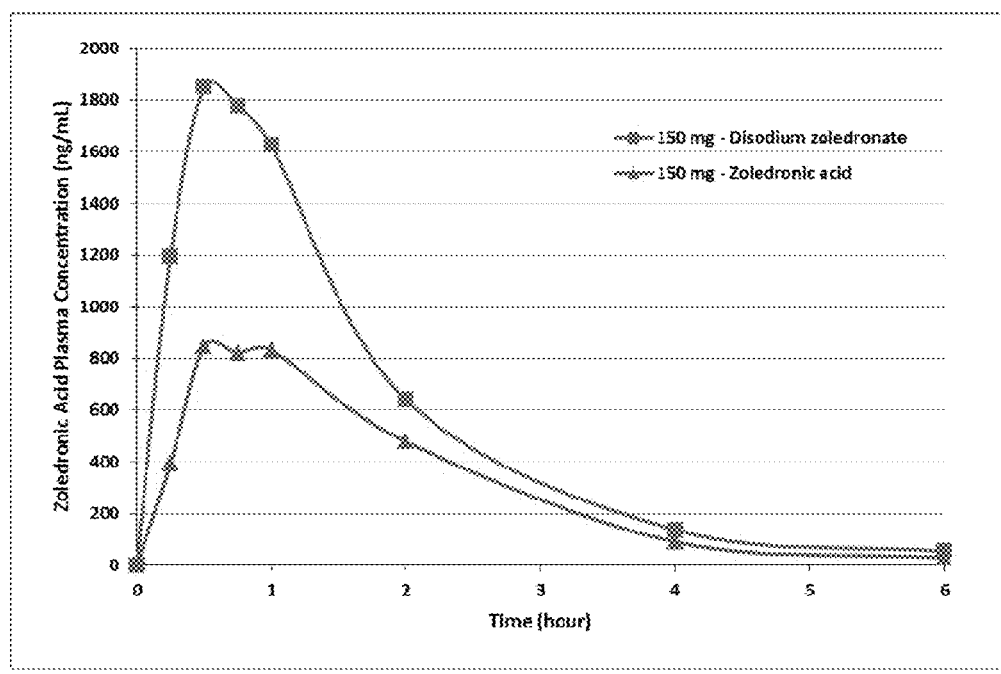
FIG. 8 depicts the plasma concentration of zoledronic acid in dogs over time after administration of 150 mg of the disodium salt form of zoledronic acid and the diacid form of zoledronic acid.

The average plasma concentrations of zoledronic acid for each group of dogs is summarized in Table 1 and illustrated in FIG. 8. Detectable plasma levels of zoledronic acid were observed for the entire 48 hours that they were measured.

TABLE 1

Zoledronic Acid plasma concentrations in beagle dogs

|  |  | Time (hour) | Plasma concentration (ng/mL) |
|---|---|---|---|
| Group 1 (N = 3) | Disodium Zoledronate Tablets (150 mg acid equivalent) | 0 | 0.00 |
|  |  | 0.25 | 1193.97 |
|  |  | 0.5 | 1852.12 |
|  |  | 0.75 | 1776.51 |
|  |  | 1 | 1626.56 |
|  |  | 2 | 640.57 |
|  |  | 4 | 136.93 |
|  |  | 6 | 53.11 |
|  |  | 8 | 26.97 |
|  |  | 12 | 13.74 |
|  |  | 24 | 6.78 |
|  |  | 48 | 5.39 |

TABLE 1-continued

Zoledronic Acid plasma concentrations in beagle dogs

|  |  | Time (hour) | Plasma concentration (ng/mL) |
|---|---|---|---|
| Group 2 (N = 3) | Zoledronic Acid Tablets (150 mg acid equivalent) | 0 | 0.00 |
|  |  | 0.25 | 390.92 |
|  |  | 0.5 | 846.19 |
|  |  | 0.75 | 819.15 |
|  |  | 1 | 831.77 |
|  |  | 2 | 477.76 |
|  |  | 4 | 90.11 |
|  |  | 6 | 28.22 |
|  |  | 8 | 15.10 |
|  |  | 12 | 6.13 |
|  |  | 24 | 3.18 |
|  |  | 48 | 1.84 |

Disodium zoledronate produced significantly higher plasma levels zoledronic acid than pure zoledronic acid, indicating improved oral absorption with the salt form. Measured using peak plasma concentrations ($C_{max}$), the disodium salt resulted in a 119% actual and 74% weight-adjusted increase in bioavailability as compared to pure zoledronic acid. Measured using area under the plasma concentration curve ($AUC_{0-\infty}$), bioavailability was 84% and 46% greater with the disodium salt than with pure zoledronic acid, on an actual and weight-adjusted basis respectively. The average $AUC_{0-\infty}$ for the disodium salt was 4073 ng·hr/mL and the average $AUC_{0-\infty}$ for the diacid was 2217 ng·hr/mL. The $AUC_{0-\infty}$ was found to be dose proportional. Thus, for beagle dogs similar to those tested, about 3 mg to about 4 mg of the disodium salt would be expected to result in an $AUC_{0-\infty}$ of about 100 ng·hr/mL, and about 7 mg to about 8 mg of the disodium salt would be expected to result in an $AUC_{0-\infty}$ of about 200 ng·hr/mL.

Example 8

Figure 9:
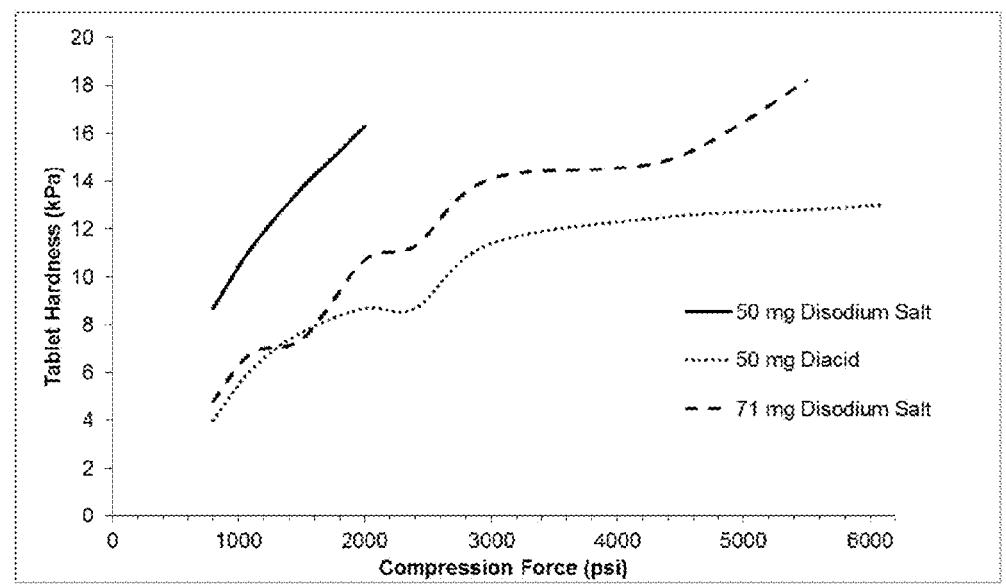
FIG. 9 depicts the compressibility of dosage forms containing zoledronic acid in the disodium salt form as compared to the diacid form.

Tablets were prepared by blending zoledronic acid, either in the form of the free acid or the disodium salt, with identical excipients. For dosage forms with a greater amount of active, the amount of the excipients was reduced proportionally to keep the weight of the tablet at about 100 mg. After blending, the ingredients were compressed at varying pressures, followed by a film coating. The resulting tablets were then tested for hardness using a Dr. Schleuniger Pharmatron 8M Tablet Hardness Tester. The results are shown in Table 2 and FIG. 9.

TABLE 2

| Compression Force (psi) | Hardness (kPa) | | |
|---|---|---|---|
|  | Diacid 50 mg | Disodium Salt 50 mg | Disodium Salt 71 mg |
| 800 | 4.0 | 8.7 | 4.8 |
| 1100 | 6.1 | 11.2 | 6.8 |
| 1500 | 7.7 | 13.7 | 7.4 |
| 2000 | 8.7 | 16.3 | 10.7 |
| 2400 | 8.7 |  | 11.3 |
| 3000 | 11.4 |  | 14.1 |
| 4400 | 12.5 |  | 14.9 |
| 5500 | 12.8 |  | 18.2 |
| 6100 | 13.0 |  |  |

The following embodiments are specifically contemplated:

Embodiment 1

A method of relieving inflammatory pain comprising administering an oral dosage form containing zoledronic acid

Embodiment 2

The method of embodiment 1, wherein the mammal is a human being that receives a total monthly dose of zoledronic acid that is about 30 mg/m² to about 700 mg/m².

Embodiment 3

The method of embodiment 2, wherein the total monthly dose is administered in 4 or 5 weekly doses.

Embodiment 4

The method of embodiment 2, wherein the total monthly dose is administered in 28 to 31 daily doses.

Embodiment 5

The method of embodiment 2, wherein the total monthly dose is administered in 5 to 10 individual doses during the month.

Embodiment 6

The method of embodiment 1, wherein the mammal is a human being that receives a total weekly dose of zoledronic acid that is about 10 mg to about 300 mg.

Embodiment 7

The method of embodiment 6, wherein the total weekly dose is a single dose, administered once a week.

Embodiment 8

The method of embodiment 6, wherein the total weekly dose is administered in 2 to 7 individual doses during the week.

Embodiment 9

The method of embodiment 1, wherein the mammal is a human being that receives a total weekly dose of zoledronic acid that is about 10 mg to about 150 mg.

Embodiment 10

The method of any preceding embodiment, wherein the mammal experiences significant pain relief more than 3 hours after administration of the dosage form.

Embodiment 11

The method of embodiment 10, wherein the mammal experiences significant pain relief during at least a part of a time from about 3 hours to about 24 hours after administration of the dosage form.

Embodiment 12

The method of embodiment 10, wherein the mammal experiences significant pain relief during at least a part of a time from about 3 hours to about 3 weeks after administration of the dosage form.

Embodiment 13

A method of relieving inflammatory pain comprising administering an oral dosage form containing zoledronic acid to a mammal in need thereof, wherein the oral dosage form contains about 10 mg/m² to about 20 mg/m² of zoledronic acid based upon the body surface area of the mammal.

Embodiment 14

The method of embodiment 13, wherein the oral dosage form contains about 15 mg/m² to about 20 mg/m² of zoledronic acid based upon the body surface area of the mammal.

Embodiment 15

A method of relieving inflammatory pain comprising orally administering to a mammal in need thereof, about 300 mg/m² to about 600 mg/m² of zoledronic acid per month to the mammal, based upon the body surface area of the mammal.

Embodiment 16

The method of embodiment 15, comprising orally administering about 450 mg/m² to about 600 mg/m² of zoledronic acid per month to the mammal, based upon the body surface area of the mammal.

Embodiment 17

The method of any preceding embodiment, wherein the mammal is not suffering from bone metastasis.

Embodiment 18

The method of any preceding embodiment, wherein the mammal is not suffering from cancer.

Embodiment 19

The method of any preceding embodiment, wherein the zoledronic acid is administered as a salt of a dianion of zoledronic acid.

Embodiment 20

A method of relieving pain associated with an arthritis comprising administering an oral dosage form containing zoledronic acid to a human being in need thereof.

Embodiment 21

The method of embodiment 20, wherein the human being receives a total monthly dose of zoledronic acid that is about 40 mg to about 2000 mg.

Embodiment 22

The method of embodiment 21, wherein the total monthly dose is administered in 4 or 5 weekly doses.

Embodiment 23

The method of embodiment 21, wherein the total monthly dose is administered in 28 to 31 daily doses.

to a mammal in need thereof, wherein the mammal receives a total monthly dose of zoledronic acid that is about 800 mg/m² or less based upon the body surface area of the mammal.

Embodiment 24

The method of embodiment 21, wherein the total monthly dose is administered in 5 to 10 individual doses during the month.

Embodiment 25

The method of embodiment 20, wherein the human being receives a total weekly dose of zoledronic acid that is about 100 mg to about 300 mg.

Embodiment 26

The method of embodiment 25, wherein the total weekly dose is a single dose, administered once a week.

Embodiment 27

The method of embodiment 25, wherein the total weekly dose is administered in 2 to 7 individual doses during the week.

Embodiment 28

The method of embodiment 20, wherein the human being receives a total weekly dose of zoledronic acid that is about 10 mg to about 100 mg.

Embodiment 29

The method of any of embodiments 20-28, wherein the human being experiences significant pain relief more than 3 hours after administration of the dosage form.

Embodiment 30

The method of embodiment 29, wherein the human being experiences significant pain relief during at least a part of a time from about 3 hours to about 24 hours after administration of the dosage form.

Embodiment 31

The method of embodiment 29, wherein the human being experiences significant pain relief during at least a part of a time from about 3 hours to about 3 weeks after administration of the dosage form.

Embodiment 32

The method of any of embodiments 20-31, wherein the dosage form contains about 10 mg/m$^2$ to about 20 mg/m$^2$ of zoledronic acid based upon the body surface area of the human being.

Embodiment 33

The method of embodiment 32, wherein the dosage form contains about 15 mg/m$^2$ to about 20 mg/m$^2$ of zoledronic acid based upon the body surface area of the human being.

Embodiment 34

The method of any of embodiments 20-33, wherein about 50 mg/m$^2$ to about 200 mg/m$^2$ of zoledronic acid is orally administered per month, based upon the body surface area of the human being.

Embodiment 35

The method of any of embodiments 20-31, wherein the dosage form contains about 80 mg/m$^2$ to about 150 mg/m$^2$ of zoledronic acid based upon the body surface area of the human being.

Embodiment 36

The method of embodiment 35, wherein about 300 mg/m$^2$ to about 1000 mg/m$^2$ of zoledronic acid is orally administered per month, based upon the body surface area of the human being.

Embodiment 37

The method of any of embodiments 20-36, wherein the human being is not suffering from bone metastasis.

Embodiment 38

The method of any of embodiments 20-37, wherein the human being is not suffering from cancer.

Embodiment 39

The method of any preceding embodiment, wherein the zoledronic acid is in the disodium salt form.

Embodiment 40

An or dosage form comprising zoledronic acid, wherein the oral bioavailability of zoledronic acid in the dosage form is about 0.01%) to about 4%.

Embodiment 41

The oral dosage form of embodiment 40, wherein the oral dosage form contains about 10 mg to about 300 mg of zoledronic acid.

Embodiment 42

The oral dosage form of embodiment 40, wherein the oral dosage form contains about 10 mg to about 50 mg of zoledronic acid.

Embodiment 43

The oral dosage form of any of embodiments 40-42, wherein the oral bioavailability of zoledronic acid in the dosage form is about 0.1% to about 2%.

Embodiment 44

A pharmaceutical product comprising more than one unit of an oral dosage form of embodiment 40.

Embodiment 45

The pharmaceutical product of embodiment 44, wherein each unit of the oral dosage form contains about 1 mg to about 50 mg of zoledronic acid.

Embodiment 46

The pharmaceutical product of embodiment 45, comprising 28, 29, 30, or 31 units of the oral dosage form, for a total of about 28 mg to about 1600 mg of zoledronic acid to be administered in about 1 month.

Embodiment 47

The pharmaceutical product of embodiment 45, comprising 85 to 95 units of the oral dosage form, for a total of about 85 mg to about 4800 mg of zoledronic acid to be administered in about 3 months.

Embodiment 48

The pharmaceutical product of embodiment 45, comprising 170 to 200 units of the oral dosage form, for a total of about 170 mg to about 10,000 mg of zoledronic acid to be administered in about 6 months.

Embodiment 49

The pharmaceutical product of embodiment 45, comprising 350 to 380 units of the oral dosage form, for a total of about 350 mg to about 19,000 mg of zoledronic acid to be administered in about 1 year.

Embodiment 50

The pharmaceutical product of embodiment 44, wherein each unit of the oral dosage form contains about 10 mg to about 300 mg.

Embodiment 51

The pharmaceutical product of embodiment 50, comprising 4 or 5 units of the oral dosage form, for a total of about 40 mg to about 1500 mg of zoledronic acid to be administered within a period of about 1 month.

Embodiment 52

The pharmaceutical product of embodiment 50, comprising 8 or 9 units of the oral dosage form, for a total of about 80 mg to about 2700 mg of zoledronic acid to be administered in about 2 months.

Embodiment 53

The pharmaceutical product of embodiment 50, comprising 12, 13 or 14 units of the oral dosage form, for a total of about 120 mg to about 4200 mg of zoledronic acid to be administered in about 3 months.

Embodiment 54

The pharmaceutical product of embodiment 50, comprising 22 to 30 units of the oral dosage form, for a total of about 220 mg to about 9000 mg of zoledronic acid to be administered in about 6 months.

Embodiment 55

The pharmaceutical product of embodiment 50, comprising 45 to 60 units of the oral dosage form, for a total of about 450 mg to about 18000 mg of zoledronic acid to be administered in about 1 year.

Embodiment 56

The pharmaceutical product of embodiment 44, comprising 1 to 10 units of the oral dosage form, wherein the product contains about 200 mg to about 2000 mg of zoledronic acid.

Embodiment 57

The oral dosage form of any preceding embodiment, wherein the zoledronic acid is in the form of a sodium salt.

Embodiment 58

The oral dosage form of any preceding embodiment, wherein the zoledronic acid is in a form that has an aqueous solubility greater than 1% (w/v).

Embodiment 59

The oral dosage form of any preceding embodiment, wherein the zoledronic acid is in a form that has an aqueous solubility of about 5% (w/v) to about 50% (w/v).

Embodiment 60

An oral dosage form comprising zoledronic acid and an excipient, wherein the zoledronic acid is in a form that has an aqueous solubility greater than 1% (w/v).

Embodiment 61

The oral dosage form of embodiment 60, wherein the zoledronic acid is in a form that has an aqueus solubility of about 5% (w/v) to about 50% (w/v).

Embodiment 62

A method of treating complex regional pain syndrome comprising administering an oral dosage form containing zoledronic acid to a mammal in need thereof.

Embodiment 63

The method of embodiment 62, wherein the mammal is a human being that receives an amount of zoledronic acid that is about 30 mg/m$^2$ to about 700 mg/m$^2$ in a period of one month or less.

Embodiment 64

The method of embodiment 63, wherein 4 or 5 weekly doses are administered in a period of one month or less.

Embodiment 65

The method of embodiment 63, wherein 28 to 31 daily doses are administered in a period of one month or less.

Embodiment 66

The method of embodiment 63, wherein 5 to 10 individual doses are administered during a period of one month or less.

Embodiment 67

The method of embodiment 63, wherein about 30 mg/m$^2$ to about 700 mg/m$^2$ of zoledronic acid is administered during only one month.

Embodiment 68

The method of embodiment 63, wherein about 30 mg/m$^2$ to about 700 mg/m$^2$ of zoledronic acid is administered in a period of one month or less for 2 or more consecutive months.

Embodiment 69

The method of embodiment 62, wherein the mammal receives about 10 mg/m$^2$ to about 30 mg/m$^2$ of zoledronic acid daily.

Embodiment 70

The method of embodiment 62, wherein the mammal is a human being that receives a total weekly dose of zoledronic acid that is about 10 mg to about 300 mg.

Embodiment 71

The method of embodiment 70, wherein the total weekly dose is a single dose, administered once a week.

Embodiment 72

The method of embodiment 70, wherein the total weekly dose is administered in 2 to 7 individual doses during the week.

Embodiment 73

The method of any of embodiments 62-72, wherein the complex regional pain syndrome is complex regional pain syndrome type I.

Embodiment 74

The method of any of embodiments 62-72, wherein the complex regional pain syndrome is complex regional pain syndrome type II.

Embodiment 75

The method of any preceding embodiment, wherein the zoledronic acid is in a salt form.

Embodiment 76

The method of any of embodiments 62-75, wherein the dosage form contains about 10 mg/m$^2$ to about 20 mg/m$^2$ of zoledronic acid based upon the body surface area of the mammal.

Embodiment 77

The method of embodiment 76, wherein the dosage form contains about 15 mg/m$^2$ to about 20 mg/m$^2$ of zoledronic acid based upon the body surface area of the mammal.

Embodiment 78

A method of treating complex regional pain syndrome, comprising administering pamidronic acid to a human being in need thereof.

Embodiment 79

A method of treating complex regional pain syndrome, comprising administering neridronic acid to a human being in need thereof.

Embodiment 80

A method of treating complex regional pain syndrome, comprising administering olpadronic acid to a human being in need thereof.

Embodiment 81

A method of treating complex regional pain syndrome, comprising administering alendronic acid to a human being in need thereof.

Embodiment 82

A method of treating complex regional pain syndrome, comprising administering incadronic acid to a human being in need thereof.

Embodiment 83

A method of treating complex regional pain syndrome, comprising administering ibandronic acid to a human being in need thereof.

Embodiment 84

A method of treating complex regional pain syndrome, comprising administering risedronic acid to a human being in need thereof.

Embodiment 85

A method of treating pain, comprising administering pamidronic acid to a human being in need thereof.

Embodiment 86

A method of treating pain, comprising administering neridronic acid to a human being in need thereof.

Embodiment 87

A method of treating pain, comprising administering olpadronic acid to a human being in need thereof.

Embodiment 88

A method of treating pain, comprising administering alendronic acid to a human being in need thereof.

Embodiment 89

A method of treating pain, comprising administering incadronic acid to a human being in need thereof.

Embodiment 90

A method of treating pain, comprising administering ibandronic acid to a human being in need thereof.

Embodiment 91

A method of treating pain, comprising administering risedronic acid to a human being in need thereof.

Embodiment 92

A method of treating arthritis pain, comprising administering pamidronic acid to a human being in need thereof.

Embodiment 93

A method of treating arthritis pain, comprising administering neridronic acid to a human being in need thereof.

Embodiment 94

A method of treating arthritis pain, comprising administering olpadronic acid to a human being in need thereof.

Embodiment 95

A method of treating arthritis pain, comprising administering alendronic acid to a human being in need thereof.

Embodiment 96

A method of treating arthritis pain, comprising administering incadronic acid to a human being in need thereof.

Embodiment 97

A method of treating arthritis pain, comprising administering ibandronic acid to a human being in need thereof.

Embodiment 98

A method of treating arthritis pain, comprising administering risedronic acid to a human being in need thereof.

Embodiment 99

A method of treating inflammatory pain, comprising administering pamidronic acid to a human being in need thereof.

Embodiment 100

A method of treating inflammatory pain, comprising administering neridronic acid to a human being in need thereof.

Embodiment 101

A method of treating inflammatory pain, comprising administering olpadronic acid to a human being in need thereof.

Embodiment 102

A method of treating inflammatory pain, comprising administering alendronic acid to a human being in need thereof.

Embodiment 103

A method of treating inflammatory pain, comprising administering incadronic acid to a human being in need thereof.

Embodiment 104

A method of treating inflammatory pain, comprising administering ibandronic acid to a human being in need thereof.

Embodiment 105

A method of treating inflammatory pain, comprising administering risedronic acid to a human being in need thereof.

Embodiment 106

A method of treating complex regional pain syndrome, comprising administering etidronic acid to a human being in need thereof.

Embodiment 107

A method of treating pain, comprising administering etidronic acid to a human being in need thereof.

Embodiment 108

A method of treating arthritis pain, comprising administering etidronic acid to a human being in need thereof.

Embodiment 109

A method of treating inflammatory pain, comprising administering etidronic acid to a human being in need thereof.

Embodiment 110

A method of treating complex regional pain syndrome, comprising administering clodronic acid to a human being in need thereof.

Embodiment 111

A method of treating pain, comprising administering clodronic acid to a human being in need thereof.

Embodiment 112

A method of treating arthritis pain, comprising administering clodronic acid to a human being in need thereof.

Embodiment 113

A method of treating inflammatory pain, comprising administering clodronic acid to a human being in need thereof.

Embodiment 114

A method of treating complex regional pain syndrome, comprising administering tiludronic acid to a human being in need thereof.

Embodiment 115

A method of treating pain, comprising administering tiludronic acid to a human being in need thereof.

Embodiment 116

A method of treating arthritis pain, comprising administering tiludronic acid to a human being in need thereof.

Embodiment 117

A method of treating inflammatory pain, comprising administering tiludronic acid to a human being in need thereof.

Embodiment 118

The method of any of embodiments 78-117, wherein the active compound is orally administered.

Embodiment 119

The method of any of embodiments 78-117, wherein the active compound is parenterally administered.

Embodiment 120

A method of enhancing the oral bioavailability of zoledronic acid comprising orally administering a dosage form containing zoledronic acid in the disodium salt form.

Embodiment 121

The method of embodiment 120, wherein the zoledronic acid in the disodium salt form provides an enhancement to bioavailability, as compared to zoledronic acid in the diacid form, which adds to any enhancement to bioavailability provided by any bioavailability-enhancing agents in the dosage form.

Embodiment 122

The method of embodiment 120, wherein the dosage form is substantially free of bioavailability-enhancing agents.

Embodiment 123

The method of embodiment 120, wherein the zoledronic acid in the disodium salt form is administered to a mammal in an amount that provides an area under the plasma concentration curve of zoledronic acid of about 4 ng·h/mL to about 2000 ng·h/mL to the mammal each time the zoledronic acid in the disodium salt is administered.

Embodiment 124

The method of embodiment 123, wherein the zoledronic acid in the disodium salt form is administered at an interval of about 3 to about 4 weeks in an amount that provides an area under the plasma concentration curve of zoledronic acid of about 100 ng·h/mL to about 2000 ng·h/mL to the mammal each time the zoledronic acid in the disodium salt form is administered.

Embodiment 125

The method of embodiment 123, wherein the zoledronic acid in the disodium salt form is administered weekly, or 3 to 5 times in a month, in an amount that provides an area under the plasma concentration curve of zoledronic acid of about 20 ng·h/mL to about 700 ng·h/mL to the mammal each time the zoledronic acid in the disodium salt form is administered.

Embodiment 126

The method of embodiment 123, wherein the zoledronic acid in the disodium salt form is administered daily in an amount that provides an area under the plasma concentration curve of zoledronic acid of about 4 ng·h/mL to about 100 ng·h/mL to the mammal each time the zoledronic acid in the disodium salt form is administered.

Embodiment 127

The method of embodiment 120, wherein the dosage form is a solid.

Embodiment 128

The method of embodiment 120, 121, 122, 123, 124, 125, 126, or 127, wherein the bioavailability of zoledronic acid is improved by at least about 20% as compared to administration of zoledronic acid in the diacid form.

Embodiment 129

The method of embodiment 120, 121, 122, 123, 124, 125, 126, 127, or 128, further comprising administering, on a molar basis, less of the zoledronic acid in the disodium salt form than would be administered of zoledronic acid in the diacid form in order to achieve the same plasma levels of zoledronic acid.

Embodiment 130

The method of embodiment 129, wherein at least about 10 mole % less of the disodium salt form is administered as compared the amount of zoledronic acid in the diacid form that would be administered in order to achieve the same plasma levels of zoledronic acid.

Embodiment 131

The method of embodiment 129, wherein the disodium salt form is administered in an amount, on a molar basis, that has a value of about $0.8n_d$ to about $1.2n_d$, wherein:

$$n_d = (b_a/b_d)(n_a)$$

wherein $b_a$ is the bioavailability of the diacid form, $b_d$ is the bioavailability of the disodium salt form, and $n_a$ is the number of moles of zoledronic acid in the diacid form that would be administered in order to achieve the same plasma levels of zoledronic acid.

Embodiment 132

The method of embodiment 131, wherein the disodium salt is administered in an amount that has a value of about $n_d$.

Embodiment 133

The method of any of embodiments 120-132, wherein the zoledronic acid is used to treat an inflammatory condition.

Embodiment 134

The method of embodiment 133, wherein the zoledronic acid is used to treat arthritis.

Embodiment 135

The method of embodiment 133, wherein the zoledronic acid is used to treat complex regional pain syndrome.

Embodiment 136

The method of any of embodiments 1-39, 62-77, and 120-135, wherein:
a first oral dosage form is administered; and
a second oral dosage form is administered;
wherein, with respect to the first oral dosage form, the second oral dosage form is administered at $10 \times T_{max}$ or greater, wherein $T_{max}$ is the time of maximum plasma concentration for the first oral dosage form.

Embodiment 137

A dosage form comprising zoledronic acid in the disodium salt form, wherein the bioavailability, in a mammal, of zoledronic acid in the disodium salt form is greater than the bioavailability of zoledronic acid in the diacid form would be in the same dosage form.

Embodiment 138

A dosage form comprising zoledronic acid in the disodium salt form, wherein the dosage form contains an amount of zoledronic acid in the disodium salt form that provides an area under the plasma concentration curve of zoledronic acid of about 4 ng·h/mL to about 2000 ng·h/mL to a human being to which the dosage form is administered.

Embodiment 139

The dosage form of embodiment 138, wherein the dosage form contains an amount of zoledronic acid in the disodium salt form that provides an area under the plasma concentration curve of zoledronic acid of about 100 ng·h/mL to about 2000 ng·h/mL to a human being to which the dosage form is administered.

Embodiment 140

The dosage form of embodiment 138, wherein the dosage form contains an amount of zoledronic acid in the disodium salt form that provides an area under the plasma concentration curve of zoledronic acid of about 20 ng·h/mL to about 700 ng·h/mL to a human being to which the dosage form is administered.

Embodiment 141

The dosage form of embodiment 138, wherein the dosage form contains an amount of zoledronic acid in the disodium salt form that provides an area under the plasma concentration curve of zoledronic acid of about 4 ng·h/mL to about 100 ng·h/mL to a human being to which the dosage form is administered.

Embodiment 142

A dosage form comprising zoledronic acid in the disodium salt form,
wherein the disodium salt form is present in a lower molar amount than would be present if the zoledronic acid were in the diacid form; and
wherein the zoledronic acid in the disodium salt form has an improved bioavailability as compared to the zoledronic acid in the diacid form to the extent that the lower molar amount of the disodium salt in the dosage form does not reduce the amount of zoledronic acid delivered to the plasma of a mammal.

Embodiment 143

The dosage form of embodiment 137, 138, 139, 140, 141, or 142, wherein the dosage form is a solid.

Embodiment 144

The dosage form of embodiment 142 or 143, wherein the bioavailability of zoledronic acid in the disodium salt form is improved by at least about 10% as compared to an otherwise identical dosage form containing zoledronic acid in the diacid form.

Embodiment 145

The dosage form of embodiment 142, 143, or 144, containing at least about 20 mole % less of the disodium salt form as compared to the amount of the zoledronic acid in the diacid form that would be present if the zoledronic acid were in the diacid form.

Embodiment 146

The dosage form of embodiment 142, wherein the disodium salt form is present in an amount, on a molar basis, that has a value of about 0.9 nd to about 1.1 nd, wherein:

$$n_d = (b_d/b_a)(n_a)$$

wherein $b_a$ is the bioavailability of the diacid form, $b_d$ is the bioavailability of the disodium salt form, and $n_a$ is the number of moles of the diacid form that would be present if the zoledronic acid were in the diacid form.

Embodiment 147

The dosage form of embodiment 146, wherein the disodium salt is administered in an amount that has a value of about $n_d$.

Embodiment 148

The method of any of embodiments 1-39, 62-77, and 120-136, wherein:
only a single oral dosage form is administered; or
a first oral dosage form is administered, and a second oral dosage form is administered after the first oral dosage form, wherein the second oral dosage form is administered before the maximum pain relieving effect of the first oral dosage form is achieved, or the second oral dosage form is administered before an observable pain relieving effect is achieved.

Embodiment 149

The method of embodiment 148, wherein the second oral dosage form is administered before an observable pain relieving effect is achieved.

Embodiment 150

The method of any of embodiments 1-39, 62-77, and 120-132, wherein a first dosage form is administered, followed by administration of a second dosage form, wherein the second dosage form is administered after the maximum pain relieving effect of the first oral dosage form is achieved, and the second oral dosage form is administered while a pain relieving effect from the first oral dosage form is observable.

Embodiment 151

The method of embodiment 148, 149, or 150, wherein the second oral dosage form is administered about 24 hours to about 28 days after the first oral dosage form is administered.

Embodiment 152

The method of any of embodiments 20-39, wherein the human being is about 30 years old to about 75 years old.

Embodiment 153

The method of any of embodiments 20-39, wherein the human being is about 1 year old to about 16 years old.

Embodiment 154

The method of any of embodiments 20-39, wherein the human being is about 80 years old to about 95 years old.

Embodiment 155

The method of any of embodiments 20-39, wherein the human being has suffered from the arthritis for at least 2 months.

Embodiment 156

The method of any of embodiments 20-39, wherein the arthritis affects, a knee, an elbow, a wrist, a shoulder, or a hip.

Embodiment 157

The method of any of embodiments 1-44, 62-133, and 144-156, wherein the mammal or human being to which the zoledronic acid is administered does not eat food or drink beverage for at least 1 hour before the zoledronic acid is administered.

Embodiment 158

The method of embodiment 157, wherein the mammal or human being to which the zoledronic acid is administered does not eat food or drink beverage for at least 2 hours before the zoledronic acid is administered.

Embodiment 159

The method of embodiment 158, wherein the mammal or human being to which the zoledronic acid is administered does not eat food or drink beverage for at least 4 hours before the zoledronic acid is administered.

Embodiment 160

The method of embodiment 159, wherein the mammal or human being to which the zoledronic acid is administered does not eat food or drink beverage for at least 6 hours before the zoledronic acid is administered.

Embodiment 161

The method of any of embodiments 157-160, wherein the mammal or human being to which the zoledronic acid is administered does not eat food or drink beverage for at least 30 minutes after the zoledronic acid is administered.

Embodiment 162

The method of embodiment 161, wherein the mammal or human being to which the zoledronic acid is administered does not eat food or drink beverage for at least 1 hour after the zoledronic acid is administered.

Embodiment 163

The method of embodiment 161, where in the mammal or human being to which the zoledronic acid is administered does not eat food or drink beverage for at least 2 hours after the zoledronic acid is administered.

Embodiment 164

The method, dosage form, or product, of any preceding embodiment, wherein the zoledronic acid in the oral dosage form has a 24 hour sustained plasma level factor of about 1 or higher.

Embodiment 165

The method, dosage form, or product, of any preceding embodiment, wherein the zoledronic acid in the oral dosage form has a 24 hour sustained plasma level factor that is higher than that of intravenously administered zoledronic acid.

Embodiment 166

The method, dosage form, or product, of any preceding embodiment, wherein the oral dosage form is a solid that has a hardness of about 5 kPa to about 20 kPa.

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of treating low back pain comprising orally administering zoledronic acid to a human being in need thereof, wherein the human being receives about 40 mg to about 300 mg of zoledronic acid per month, and wherein the human being experiences pain relief that lasts for a duration of at least 48 hours, and the human being receives zoledronic acid no more often than once daily.

2. The method of claim 1, wherein the zoledronic acid is administered in an amount and frequency that results in an AUC of zoledronic acid, over a four week period, that is about 100 ng·h/mL to about 2000 ng·h/mL.

3. The method of claim 2, wherein the zoledronic acid is administered once a month, or less frequently.

4. The method of claim 2, wherein zoledronic acid is administered for only 1 to 3 months.

5. The method of claim 3, wherein the mammal experiences pain relief at least 3 weeks after a dose of zoledronic acid is administered.

6. The method of claim 2, wherein the zoledronic acid is administered weekly.

7. The method of claim 1, wherein the zoledronic acid is administered 2 to 5 times in a month.

8. The method of claim 1, wherein the zoledronic acid is administered daily.

9. The method of claim 1, wherein human being to which the zoledronic acid is administered does not eat food or drink beverage for at least 1 hour before the zoledronic acid is administered.

10. The method of claim 1, wherein the low back pain is related to vertebral change.

11. The method of claim 1, wherein the zoledronic acid is administered in an amount and frequency that results in an AUC of zoledronic acid, over a one week period, that is about 20 ng·h/mL to about 500 ng·h/mL.

12. The method of claim 1, wherein the zoledronic acid is administered in a solid dosage form having a hardness of about 5 kPa to about 20 kPa.

13. The method of claim 1, wherein the zoledronic acid is administered in a solid dosage form that contains at least about 50% (w/w) of zoledronic acid.

14. The method of claim 1, wherein the zoledronic acid is administered daily, and a daily dose contains an amount of zoledronic acid that results in an AUC of zoledronic acid that is about 4 ng·h/mL to about 30 ng·h/mL.

15. The method of claim 1, wherein the human being to which the zoledronic acid is administered does not eat food or drink beverage for at least 30 minutes after the zoledronic acid is administered.

* * * * *

UNITED STATES PATENT AND TRADEMARK OFFICE
CERTIFICATE OF CORRECTION

| | |
|---|---|
| PATENT NO. | : 9,034,889 B2 |
| APPLICATION NO. | : 14/279229 |
| DATED | : May 19, 2015 |
| INVENTOR(S) | : Herriot Tabuteau |

It is certified that error appears in the above-identified patent and that said Letters Patent is hereby corrected as shown below:

Title page:

At Item (57), line 3, "bioavailabilty" should read --bioavailability--

In the specification:

In column 1, line 12, "embodiments" should read --claims--

In column 4, line 38, "arthropaties" should read --arthropathies--

In column 4, line 44, "75 years old," should read --75 years,--

In column 4, line 51, "affects, a knee" should read --affects a knee--

In column 7, line 52, "bioavailabity" should read --bioavailability--

In column 11, line 8, "daily or dose" should read --daily oral dose--

In column 11, line 23, "weeky" should read --weekly--

In column 13, line 17, "the or bioavailability" should read --the oral bioavailability--

In column 14, line 27, "Prosolv" should read --PROSOLV(R)--

In column 14, line 42, "Aerosil" should read --AEROSIL(R)--

In column 14, lines 56 and 65, "or dosage" should read --oral dosage--

In column 15, line 36, "Sprague-Dawley" should read --SPRAGUE-DAWLEY(R)--

In column 18, line 58, "Example 6" should read --Example 4--

In column 18, line 66, "sonification" should read --sonication--

Signed and Sealed this
Fifth Day of July, 2016

Michelle K. Lee
*Director of the United States Patent and Trademark Office*

CERTIFICATE OF CORRECTION (continued)
U.S. Pat. No. 9,034,889 B2

In the specification:

In column 19, line 14, "Example 7" should read --Example 5--

In column 20, line 36, "Example 8" should read --Example 6--

In column 24, line 32, "An or dosage" should read --An oral dosage--

In column 26, line 32, "aqueus" should read --aqueous--

In column 35, line 40, "affects, a" should read --affects a--